(12) United States Patent
Hoffmeyer et al.

(10) Patent No.: US 9,309,187 B2
(45) Date of Patent: Apr. 12, 2016

(54) EP2 RECEPTOR AGONISTS

(71) Applicant: TAKEDA GMBH, Constance (DE)

(72) Inventors: Angelika Hoffmeyer, Constance (DE); Rainer Boer, Constance (DE); Manuela Hessmann, Grossensee (DE); Andreas Pahl, Heidelberg (DE); Torsten Dunkern, Juchen (DE); Simone Hartung, Allensbach (DE); Christof Zitt, Constance (DE); Jurgen Volz, Radolfzell (DE); Christiane Praechter, Hamburg (DE); Mahindra Makhija, Mumbai (IN); Hiteshkumar Jain, Mumbai (IN); Sandip Gavade, Mumbai (IN); Arati Prabhu, Mumbai (IN); Manojkumar Tiwari, Maharashtra (IN); Ashish Keche, Maharashtra (IN); Sarvesh Patel, Maharashtra (IN)

(73) Assignee: Takeda GmbH, Constance (DE)

( * ) Notice: Subject to any disclaimer, the term of this patent is extended or adjusted under 35 U.S.C. 154(b) by 0 days.

(21) Appl. No.: 14/397,319

(22) PCT Filed: Apr. 30, 2013

(86) PCT No.: PCT/EP2013/058947
§ 371 (c)(1),
(2) Date: Oct. 27, 2014

(87) PCT Pub. No.: WO2013/164326
PCT Pub. Date: Nov. 7, 2013

(65) Prior Publication Data
US 2015/0080400 A1    Mar. 19, 2015

(30) Foreign Application Priority Data

May 3, 2012  (IN) .......................... 1379/MUM/2012
Jun. 20, 2012  (EP) ..................................... 12172673

(51) Int. Cl.

| | |
|---|---|
| C07D 265/30 | (2006.01) |
| C07C 233/81 | (2006.01) |
| C07C 233/75 | (2006.01) |
| C07C 235/66 | (2006.01) |
| C07C 237/40 | (2006.01) |
| C07C 237/42 | (2006.01) |
| C07D 295/155 | (2006.01) |
| A61K 31/196 | (2006.01) |
| A61K 31/27 | (2006.01) |
| A61K 31/4453 | (2006.01) |
| A61K 31/495 | (2006.01) |
| A61K 31/5375 | (2006.01) |
| A61K 45/06 | (2006.01) |
| C07C 237/52 | (2006.01) |
| C07C 271/42 | (2006.01) |

(52) U.S. Cl.
CPC ............. *C07C 233/81* (2013.01); *A61K 31/196* (2013.01); *A61K 31/27* (2013.01); *A61K 31/4453* (2013.01); *A61K 31/495* (2013.01); *A61K 31/5375* (2013.01); *A61K 45/06* (2013.01); *C07C 233/75* (2013.01); *C07C 235/66* (2013.01); *C07C 237/40* (2013.01); *C07C 237/42* (2013.01); *C07C 237/52* (2013.01); *C07C 271/42* (2013.01); *C07D 295/155* (2013.01)

(58) Field of Classification Search
CPC ............. C07D 295/023; C07D 265/30; C07D 295/027; C07D 213/74; C07C 213/02
USPC ........................................ 544/106; 514/237.8
See application file for complete search history.

(56) References Cited

FOREIGN PATENT DOCUMENTS

| | | | |
|---|---|---|---|
| CN | 101495452 A | 7/2009 | |
| WO | 2005/080367 A1 | 9/2005 | |
| WO | WO 2005080367 A1 * | 9/2005 | ............ C07C 233/75 |
| WO | 2007/017687 A2 | 2/2007 | |
| WO | WO 2007017687 A2 * | 2/2007 | ............ C07C 233/81 |
| WO | 2008/015517 A2 | 2/2008 | |
| WO | 2009/098458 A2 | 8/2009 | |

OTHER PUBLICATIONS

Buckley, et al., "EP4 Receptor as a New Target for Bronchodilator Therapy", Thorax, 2011, vol. 66, pp. 1029-1035.
Forselles, et al., "In Vitro and in Vivo Characterization of PF-04418948, a Novel, Potent and Selective Prostaglandin EP2 Receptor Antagonist", British Journal of Pharmacology, 2011, vol. 164, pp. 1847-1856.

(Continued)

*Primary Examiner* — Nyeemah A Grazier
*Assistant Examiner* — Sagar Patel
(74) *Attorney, Agent, or Firm* — Nath, Goldberg & Meyer; Joshua B. Goldberg; Scott H. Blackman

(57) ABSTRACT

The compounds of formula (1)

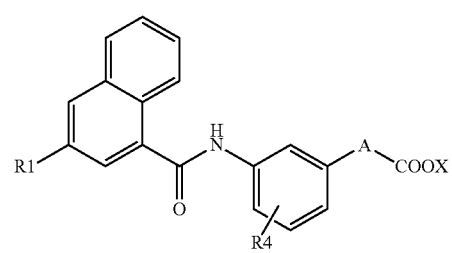

(1)

in which R1, R4, A and X have the meanings as given in the description, are novel effective EP2 agonists.

20 Claims, No Drawings

(56) References Cited

OTHER PUBLICATIONS

Gauvreau, et al., "Protective Effects of Inhaled PGE2 on Allergen-Induced Airway Responses and Airway Inflammation", AM J Respir Crit Care Med, 1999, vol. 159, pp. 31-36.

Kolodsick, et al., "Prostaglandin E2 Inhibits Fibroblast to Myofibroblast Transition Via E. Prostanoid Receptor 2 Signaling and Cyclic Adenosine Monophosphate Elevation", Am. J. Respir. Cell Mol. Biol., 2003, vol. 29, pp. 537-544.

Takahashi, et al., "Prostaglandin E2 Inhibits Advanced Glycation End Product-Induced Adhesion Molecule Expression, Cytokine Production, and Lymphocyte Proliferation in Human Peripheral Blood Mononuclear Cells", The Journal of Pharmacology and Experimental Therapeutics, 2009, vol. 331, No. 2, pp. 656-670.

Vancheri, et al., "The Lung as a privileged Site for the Beneficial Actions of PGE2", Trends in Immunology, Jan. 2004, vol. 25, No. 1, pp. 40-46.

White, et al., "Prostaglandin E2 Mediates IL-1B-Related Fibroblast Mitogenic Effects in Acute Lung Injury Through Differential Utilization of Prostanoid Receptors", The Journal of Immunology, 2008, vol. 180, pp. 637-646.

* cited by examiner

EP2 RECEPTOR AGONISTS

This application is filed under 35 U.S.C. 371 as the U.S. national stage of PCT/EP2013/058947, filed Apr. 30, 2013, which claims priority to 1379/MUM/2012, filed May 3, 2012 and EP 12172673.1, filed Jun. 20, 2012.

FIELD OF APPLICATION OF THE INVENTION

The invention relates to novel EP2 receptor agonists according to formula (1), which are used in the pharmaceutical industry for the manufacture of pharmaceutical compositions.

KNOWN TECHNICAL BACKGROUND

Prostaglandins (PGs) are part of the prostanoid family and their receptors fall into five different classes—DP, EP, FP, IP and TP—based on their sensitivity to the five naturally occurring prostanoids, $PGD_2$, $PGE_2$, $PGF_{2\alpha}$, $PGI_2$ and $TxA2$, respectively (Coleman, R. A., Prostanoid Receptors, IUPHAR compendium of receptor characterization and classification, $2^{nd}$ edition, 338-353, ISBN 0-9533510-3-3, 2000). EP receptors (for which the endogenous ligand is $PGE_2$) have been subdivided into four types termed EP1, EP2, EP3 and EP4.

The international patent applications WO2005080367 and WO 2007017687 describe various EP2 receptor agonists and the use thereof for the treatment of conditions like inflammatory disorders, asthma and chronic obstructive pulmonary disease.

DESCRIPTION OF THE INVENTION

It has now been found that the compounds according to formula (1), which are described in greater details below, have surprising and particularly advantageous properties.

The invention relates to a compound of formula (1)

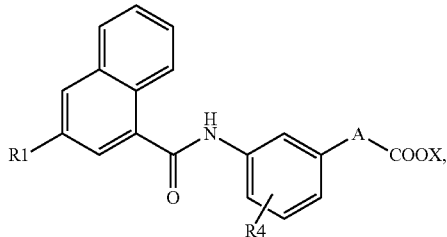

(1)

wherein
A is —O—$CH_2$—, —C≡C— or —$CH_2$—$CH_2$—,
X is hydrogen or 1-4C-alkyl,
R1 is unsubstituted phenyl, phenyl substituted by R2 or phenyl substituted by R2 and R3, wherein
R2 is —$(CH_2)_n$—OH, —$(CH_2)_q$$NH_2$, halogen, —$CH_2$—NH(CO)R21, —O—(CO)—N(R22)(R23) or

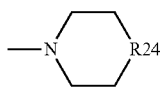

wherein
n is an integer from 0 to 4,
q is an integer from 1 to 4,
R21 is 1-4C-alkyl,
R22 is hydrogen or 1-2C-alkyl,
R23 is hydrogen or 1-2C-alkyl,
R24 is NR25, $CH_2$, O or S
wherein
R25 is hydrogen or 1-2C-alkyl,
R3 is —$(CH_2)_p$—OH,
wherein
p is an integer from 0 to 2,
R4 is hydrogen or halogen,
or a salt, a solvate or a solvate of the salt of the compound.

1-4C-Alkyl is a straight-chain or branched alkyl group having 1 to 4 carbon atoms. Examples are butyl, isobutyl, sec-butyl, tert-butyl, propyl, isopropyl, ethyl and methyl.

1-2C-Alkyl is a straight-chain alkyl group having 1 to 2 carbon atoms. Examples are ethyl and methyl.

Halogen stands for fluorine, chlorine, bromine or iodine, with fluorine, chlorine or bromine being preferred and with fluorine and chlorine being more preferred.

It is to be understood that the substituent R4 can be attached in 2-position, 3-position or 4-position to the phenyl ring, preferably in 4-position to the phenyl ring.

Exemplary phenyl rings substituted by R4, which may be mentioned, are 4-fluoro-phenyl and 4-chlorophenyl or R4 represents hydrogen resulting in an unsubstituted phenyl.

It is further to be understood that the substituent R2 can be attached in 2-, 3- or 4-position to the phenyl ring, preferably, R2 can be attached in 2- or in 3-position to the phenyl ring.

Furthermore, if the phenyl ring is substituted by R2 and R3, these substitutents can be attached in 2- and 3-position, in 2- and 4-position, in 2- and 5-position, in 2- and 6-position, 3- and 4-position, in 3- and 5-position and in 3- and 6-position to the phenyl ring. Preferably, R2 and R3 can be attached in 3- and 5-position to the phenyl ring.

Exemplary phenyl rings substituted by R2 or substituted by R2 and R3, which may be listed, are 2-fluoro-phenyl, 3-fluoro-phenyl, 3-aminomethyl-phenyl, 2-hydroxymethyl-phenyl, 3-hydroxymethyl-phenyl, 3-acetylaminomethyl-phenyl, 3-hydroxy-phenyl, 3-piperazin-1-yl-phenyl, 3-morpholin-4-yl-phenyl, 3-piperidin-1-yl-phenyl, 3-(dimethylcarbamoyl)oxy-phenyl or 3-fluoro-5-hydroxyphenyl.

A salt of a compound of the invention includes all acid addition salts comprising the customarily used pharmacologically acceptable inorganic and organic acids. Such suitable salts are salts with acids such as hydrochloric acid, hydrobromic acid, phosphoric acid, nitric acid, sulphuric acid, acetic acid, citric acid, D-gluconic acid, benzoic acid, 2-(4-hydroxy-benzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid. These acids are employed in an equimolar quantitative ratio or one differing therefrom in the preparation of a salt depending on whether a mono- or polybasic acid is concerned.

A salt of a compound of the invention can also represent a salt with a base, including, but not limited to, lithium, sodium, potassium, calcium, aluminum, magnesium, titanium, ammonium, meglumine and guanidinium salts.

The above salts include water-insoluble and water-soluble salts, wherein water-soluble salts are preferably employed. Furthermore, salts, which are pharmacologically acceptable, are preferred.

Pharmacologically non-acceptable salts, which can be obtained for example as process products during the preparation of the compounds according to the invention on an industrial scale, are converted into pharmacologically acceptable salts by processes known to the person skilled in the art.

The term "solvate" is used herein in the conventional sense to refer to a complex of solute, e.g. a compound of the invention or a salt of a compound of the invention, and solvent. If the solvent is water, the solvate may be conveniently referred to as a hydrate, for example, a monohydrate, a dihydrate, a trihydrate and so forth.

In a preferred embodiment, the invention relates to a compound of formula (1), wherein
A is —O—CH$_2$—, —C≡C— or —CH$_2$—CH$_2$—,
X is hydrogen or 1-2C-alkyl,
R1 is unsubstituted phenyl, phenyl substituted by R2 or phenyl substituted by R2 and R3, wherein
R2 is —(CH$_2$)$_n$—OH, —(CH$_2$)$_q$NH$_2$, halogen, —CH$_2$—NH(CO)R21, —O—(CO)—N(R22)(R23) or

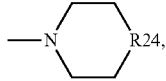

wherein
n is an integer from 0 to 2,
q is 1 or 2
R21 is 1-2C-alkyl,
R22 is hydrogen or 1-2C-alkyl,
R23 is hydrogen or 1-2C-alkyl,
R24 is NR25, CH$_2$, O or S,
wherein
R25 is hydrogen,
R3 is —(CH$_2$)$_p$—OH,
wherein
p is 0 or 1,
R4 is hydrogen or halogen,
or a salt, a solvate or a solvate of the salt of the compound.

In another preferred embodiment of the invention, the invention relates to a compound according to formula (1), wherein
A is —O—CH$_2$—, —C≡C— or —CH$_2$—CH$_2$—,
X is hydrogen or 1-2C-alkyl,
R1 is unsubstituted phenyl, phenyl substituted by R2 or phenyl substituted by R2 and R3, wherein
R2 is —(CH$_2$)$_n$—OH, —(CH$_2$)$_q$NH$_2$, halogen, —CH$_2$—NH(CO)R21, —O—(CO)—N(R22)(R23) or

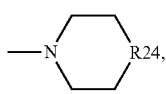

wherein
n is an integer from 0 to 2,
q is 1
R21 is 1-2C-alkyl,
R22 is 1-2C-alkyl,
R23 is 1-2C-alkyl,
R24 is —NR25, CH$_2$, O or S
wherein
R25 is hydrogen,
R3 is —(CH$_2$)$_p$—OH,
wherein
p is 0,
R4 is hydrogen, fluorine, chlorine or bromine,
or a salt, a solvate or a solvate of the salt of the compound.

In yet another preferred embodiment, the invention relates to a compound of formula (1), wherein
A is —O—CH$_2$—, —C≡C— or —CH$_2$—CH$_2$—,
X is hydrogen or 1-2C-alkyl,
R1 is unsubstituted phenyl, phenyl substituted by R2 or phenyl substituted by R2 and R3,
wherein
R2 is —(CH$_2$)$_n$—OH, —(CH$_2$)$_q$NH$_2$, halogen, —CH$_2$—NH(CO)R21, —O—(CO)—N(R22)(R23) or

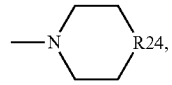

wherein
n is an integer from 0 to 2,
q is 1,
R21 is 1-2C-alkyl,
R22 is 1-2C-alkyl,
R23 is 1-2C-alkyl,
R24 is NR25, CH$_2$, O or S
wherein
R25 is hydrogen,
R3 is —(CH$_2$)$_p$—OH,
wherein
p is 0,
R4 is hydrogen, fluorine, chlorine or bromine,
or a salt, a solvate or a solvate of the salt of the compound.

In yet another preferred embodiment, the invention relates to a compound of formula (1), wherein
A is —O—CH$_2$—, —C≡C— or —CH$_2$—CH$_2$—,
X is hydrogen or 1-2C-alkyl,
R1 is unsubstituted phenyl, phenyl substituted by R2 or phenyl substituted by R2 and R3,
wherein
R2 is —(CH$_2$)$_n$—OH, fluorine, —CH$_2$—NH(CO)R21, —O—(CO)—N(R22)(R23) or

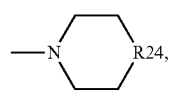

wherein
n is 0 or 1,
R21 is methyl,
R22 is methyl,
R23 is methyl,
R24 is NR25, CH$_2$ or 0,
wherein
R25 is hydrogen,
R3 is —(CH$_2$)$_p$—OH,
wherein
p is 0,
R4 is hydrogen, fluorine or chlorine,
or a salt, a solvate or a solvate of the salt of the compound.

In a further preferred embodiment, the invention relates to a compound of formula (1) or a salt, a solvate or a solvate of the salt of the compound, wherein A is —C≡C— and X, R1 and R4 are as defined above.

In a further preferred embodiment, the invention relates to a compound of formula (1) or a salt, a solvate or a solvate of the salt of the compound, wherein A is —C≡C—, X and R4 are as defined above and R1 represents an unsubstituted phenyl.

In a further preferred embodiment, the invention relates to a compound of formula (1) or a salt, a solvate or a solvate of the salt of the compound, wherein A is —C≡C—, R1 represents an unsubstituted phenyl, R4 is hydrogen, fluorine or chlorine and is preferably attached in 4-position to the phenyl ring, and X is preferably hydrogen.

In a further preferred embodiment, the invention relates to a compound of formula (1) or a salt, a solvate or a solvate of the salt of the compound, wherein A is —C≡C—, X and R4 are as defined above and R1 represents a phenyl substituted either by R2 or by R2 and R3, wherein R2 and R3 are as defined above.

In a further preferred embodiment, the invention relates to a compound of formula (1) or a salt, a solvate or a solvate of the salt of the compound, wherein A is —C≡C—, R4 is hydrogen, fluorine or chlorine, preferably fluorine, and is preferably attached in 4-position to the phenyl ring, X is preferably hydrogen and R1 represents a phenyl substituted either by R2 or by R2 and R3, wherein R2 and R3 are as defined above. If, R1 is a phenyl substituted by R2, R2 represents fluorine or chlorine, preferably fluorine, aminomethyl, hydroxymethyl, (dimethylcarbamoyl)oxy, acetylaminomethyl, piperazin-1-yl, morpholin-4-yl or piperidin-1-yl. R2 is attached in 2-, in 3- or in 4-position to the phenyl ring, preferably in 2- or in 3-position to the phenyl ring. If, R1 is a phenyl substituted by R2 and R3, R2 is hydroxy and R3 represents fluorine or chlorine, preferably fluorine. In this case, R2 and R3 are attached in 3- and 5-position to the phenyl ring.

In yet a further preferred embodiment, the invention relates to a compound of formula (1) or a salt, a solvate or a solvate of the salt of the compound, wherein A is —O—CH$_2$— and X, R1 and R4 are as defined above.

In a further preferred embodiment, the invention relates to a compound of formula (1) or a salt, a solvate or a solvate of the salt of the compound, wherein A is —O—CH$_2$—, X and R4 are as defined above and R1 represents an unsubstituted phenyl.

In a further preferred embodiment, the invention relates to a compound of formula (1) or a salt, a solvate or a solvate of the salt of the compound, wherein A is —O—CH$_2$—, R1 represents an unsubstituted phenyl, R4 is hydrogen, fluorine or chlorine and is preferably attached in 4-position to the phenyl ring, and X is preferably hydrogen.

In yet a further preferred embodiment, the invention relates to a compound of formula (1) or a salt, a solvate or a solvate of the salt of the compound, wherein A is —CH$_2$—CH$_2$— and X, R1 and R4 are as defined above.

In a further preferred embodiment, the invention relates to a compound of formula (1) or a salt, a solvate or a solvate of the salt of the compound, wherein A is —CH$_2$—CH$_2$—, X and R4 are as defined above and R1 represents an unsubstituted phenyl.

In a further preferred embodiment, the invention relates to a compound of formula (1) or a salt, a solvate or a solvate of the salt of the compound, wherein A is —CH$_2$—CH$_2$—, R1 represents an unsubstituted phenyl, R4 is hydrogen, fluorine or chlorine, preferably fluorine, and is preferably attached in 4-position to the phenyl ring, and X is preferably hydrogen.

In a further preferred embodiment, the invention relates to a compound of formula (1) or a salt, a solvate or a solvate of the salt of the compound, wherein A is —CH$_2$—CH$_2$—, X and R4 are as defined above and R1 represents a phenyl substituted by R2, wherein R2 is defined as above.

In a further preferred embodiment, the invention relates to a compound of formula (1) or a salt, a solvate or a solvate of the salt of the compound, wherein A is —CH$_2$—CH$_2$—, R4 is hydrogen, fluorine or chlorine, preferably fluorine, and is preferably attached in 4-position to the phenyl ring, X is preferably hydrogen and R1 represents a phenyl substituted by R2, wherein R2 represents fluorine or chlorine, preferably fluorine and wherein R2 is attached in 2-, in 3- or in 4-position to the phenyl ring, preferably in 2- or in 3-position to the phenyl ring.

As will be appreciated by persons skilled in the art, the invention is not limited to the particular embodiments described herein, but covers all modifications that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples, represent preferred embodiments of the invention.

EXAMPLES

All reagents were obtained from commercial sources and were used without further purification unless stated otherwise. Tetrahydrofuran (THF) was distilled from sodium-benzophenone. Flash column chromatography was performed with Rankem Silica Gel (100-200 mesh size). Thin layer chromatography (TLC) was performed on Merck pre-coated TLC aluminum sheets with Silica Gel 60 F254. The $^1$H NMR spectra were recorded on a Bruker Avance 300 MHz spectrometer, and chemical shifts (δ) are given in ppm and are referenced to the corresponding solvent residual peak. The spectral splitting patterns are indicated as follows: s, singlet; d, doublet; t, triplet; q, quartet; dd, doublet of doublets; dt, doublet of triplets; m, multiplet, br, broad. The Liquid chromatography/electrospray mass spectrometry (LC/ES-MS) analysis was performed using a Thermo Finnigan LCQ Advantage Max spectrometer. Gaschromatography-mass spectrometry (GC-MS) analysis was carried out on a Thermo Focus GC spectrometer. High-resolution mass spectra were obtained using electrospray ionization (ESI) technique on a Liquid chromatography-mass spectrometry detector/time of flight (LC-MSD/TOF) system by Agilent.

Method 1:
Reaction mixtures and products were analyzed by reverse phase High Performance Liquid Chromatography (HPLC) on a Waters Acquity instrument using a 2.1×50 mm Waters BEH C18 column. Solvent composition consisted of 0.1% aqueous ammonia and acetonitrile with a flow rate of 0.613 mL/min on gradient mode.

Method 2:
Reaction mixtures and products were analyzed by reverse phase HPLC on a Thermo Accela instrument using a 2.1×50 mm Agilent Zorbax Eclipse XDB C18 column. Solvent composition 0.1% acetic acid and acetonitrile with flow rate of 0.6 mL/min on gradient mode.

Preparative HPLC was carried out on Waters 2767 auto purification instrument using a 50×100 mm Waters XTerra Prep MS C18 OBD column. Solvent composition was 0.1% aqueous ammonia and acetonitrile with a flow rate of 117 mL/min on gradient mode or with solvent composition consisting of 0.1% acetic acid and acetonitrile with a flow rate of 117 mL/min on gradient mode.

The chemical names have been generated using the software ISIS, version 2.5 SP4.

The following examples illustrate the invention in greater detail, without restricting it. Further compounds according to the invention, of which the preparation is not explicitly described, can be prepared in an analogous way.

The example numbers, compounds numbers as being used in the reaction schemes and the specific definition of the substituents of the corresponding examples according to formula (1) are listed in the following Table 1.

TABLE 1

| Example no. | Compound no. | R1 | R2 | R3 | R4 | A | X |
|---|---|---|---|---|---|---|---|
| 1 | 6a | unsubstituted phenyl | — | — | H | —CH=CH— | H |
| 2 | 6b | unsubstituted phenyl | — | — | 4-F | —CH=CH— | H |
| 3 | 6c | unsubstituted phenyl | — | — | 4-Cl | —CH=CH— | H |
| 4 | 9a | unsubstituted phneyl | — | — | H | —O—CH$_2$— | H |
| 5 | 9b | unsubstituted phenyl | — | — | 4-F | —O—CH$_2$— | H |
| 6 | 9c | unsubstituted phenyl | — | — | 4-Cl | —O—CH$_2$— | H |
| 7 | 11a | unsubstituted phenyl | — | — | H | —CH$_2$—CH$_2$— | H |
| 8 | 11b | unsubstituted phenyl | — | — | 4-F | —CH$_2$—CH$_2$— | H |
| 9 | 17a | substituted phenyl | 2'-F | — | 4-F | —CH=CH— | H |
| 10 | 17b | substituted phenyl | 3'-F | — | 4-F | —CH=CH— | H |
| 11 | 17c | substituted phenyl | 4'-F | — | 4-F | —CH=CH— | H |
| 12 | 17d | substituted phenyl | 3'-CH$_2$NH$_2$ | — | 4-F | —CH=CH— | H |
| 13 | 17e | substituted phenyl | 2'-CH$_2$OH | — | 4-F | —CH=CH— | H |
| 14 | 17f | substituted phenyl | 3'-CH$_2$OH | — | 4-F | —CH=CH— | H |
| 15 | 17g | substituted phenyl | 3'-OH | 5'-F | 4-F | —CH=CH— | H |
| 16 | 18 | substituted phenyl | 2'-F | — | 4-F | —CH$_2$—CH$_2$— | H |
| 17 | 20 | substituted phenyl | 3'-F | — | 4-F | —CH$_2$—CH$_2$— | H |
| 18 | 22 | substituted phenyl | 3'-CH$_2$NH(CO)CH$_3$ | — | 4-F | —CH=CH— | H |
| 19 | 25a | substituted phenyl | 3'-OH | — | H | —CH=CH— | H |
| 20 | 25b | substituted phenyl | 3'-piperazinyl | — | H | —CH=CH— | H |
| 21 | 28 | substituted phenyl | 3'-morpholinyl | — | H | —CH=CH— | H |
| 22 | 29 | substituted phenyl | 3'-piperidinyl | — | 4-F | —CH=CH— | H |
| 23 | 27 | substituted phenyl | 3'—O—(CO)N(CH$_3$)$_2$ | — | H | —CH=CH— | H |

The examples no. 1 to 3 (corresponding to compounds no. 6a to 6c) according to this invention can be synthesized according to the procedure as depicted in reaction scheme 1.

Reaction Scheme 1:

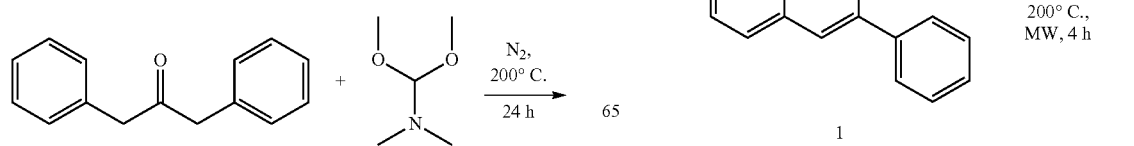

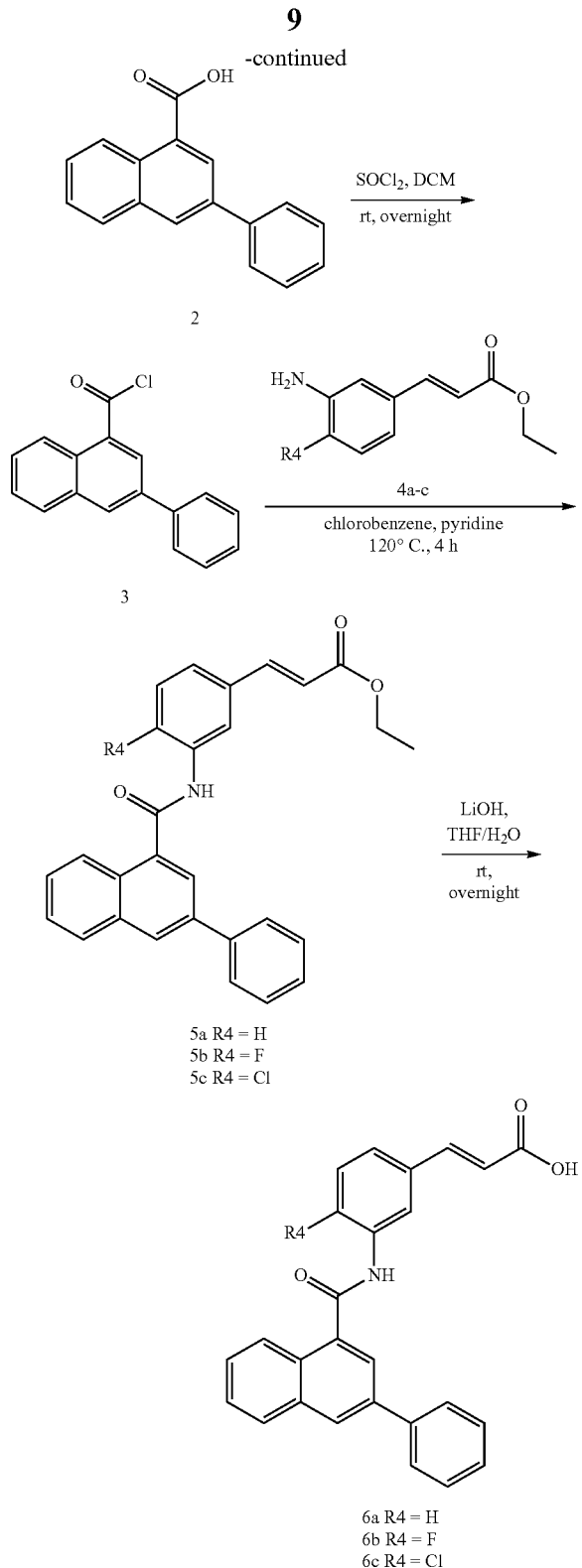

lowed by addition of appropriate cinnaminate derivatives 4a-c (0.8-1 equivalents) and 0.5-1 mL pyridine. The reaction mixture was heated at 110-130° C. for 4-6 h. The reaction mixture was evaporated to dryness and extracted with EtOAc; the organic layer was washed with brine and dried over $Na_2SO_4$ and the solvent evaporated to dryness to afford 5a-c after silica gel column chromatography.

General Procedure for the Synthesis of Compounds 6a-c

Compound 5a-c (1 equivalent) was dissolved in $THF/H_2O$ (1:1) mixture. $LiOH.H_2O$ (3-5 equivalent) was added to the reaction mixture and stirred at room temperature overnight. At this point analysis by TLC indicated the starting material has been consumed. The reaction mixture was concentrated under vacuum to dryness. The resulting residue was adjusted to pH 4-5 with dilute HCl and the resulting suspension was stirred for some time following which the solid formed was filtered and washed with 50-60% ethyl acetate/petroleum ether mixture. The residue was dried under vacuum for 3-6 h to afford 6a-c as white solids.

Example 1 (Compound 6a)

(2E)-3-(3-{[(3-phenylnaphthalen-1-yl)carbonyl]amino}phenyl)prop-2-enoic acid i) N-(Dimethylamino)-2-phenyl-4-naphthalenecarboxamide (1)

Method A: Diphenylacetone (0.173 mol) and N,Ndimethylformamide dimethyl acetal (4.28 mol) were heated in a steel autoclave at 200° C. for 24 h (hour(s)) under nitrogen atmosphere; the reaction mixture was then diluted with a mixture of $Et_2O$/hexane (1:5) and stirred for 1 h. The precipitate was filtered, washed with hexane and dried to afford 1 as white solid.

$^1$H NMR (DMSO-d6) δ 8.25 (s, 1H), 7.98-8.07 (m, 1H), 7.64-7.84 (m, 4H), 7.34-7.58 (m, 5H), 3.02-3.23 (m, 3H), 2.68-2.77 (m, 3H).

LC-ESMS m/z 276.25 (M+1)$^+$; HPLC 99.75%; Yield=52% ii) 2-Phenyl-4-naphthalenecarboxylic Acid (2)

Method B: N-(Dimethylamino)-2-phenyl-4-naphthalenecarboxamide 1 (0.18 mol) and 85% KOH pellets (0.54 mol) were heated in ethylene glycol (750 mL) at 200° C. for 4 h; the mixture was then carefully diluted with ice water and neutralized with conc. HCl and extracted with EtOAc; the organic layer was washed with brine and dried over $Na_2SO_4$ and the solvent evaporated to dryness to afford 2 as a white solid.

$^1$H NMR (DMSO-d6) δ 13.30 (br. s., 1H), 8.81-8.88 (m, 1H), 8.41-8.50 (m, 2H), 8.07-8.15 (m, 1H), 7.82-7.89 (m, 2H), 7.51-7.68 (m, 4H), 7.40-7.47 (m, 1H).

LC-ESMS m/z 247.08 [M−1]$^−$; HPLC; 99%; Yield=84%.

iii) Ethyl(2E)-3-(3-{[(3-phenylnaphthalen-1-yl)carbonyl]amino}phenyl)prop-2-enoate (5a)

Method D: Compound 2 (1 equivalent) was taken in $SOCl_2$ (10 mL) and the resulting suspension was refluxed for 4-6 h. The excess $SOCl_2$ was removed under vacuum and toluene (20 mL) was added to the residue and again evaporated under vacuum to dryness. Chlorobenzene (10 mL) was added to the resulting residue under $N_2$ atmosphere followed by addition of ethyl(2E)-3-(3-aminophenyl)prop-2-enoate (4a) (0.8 equivalents) and 0.5 mL pyridine. The reaction mixture was General Procedure for the Synthesis of Compounds 5a-c Compound 2 (1 equivalent) was taken in $SOCl_2$ (10-15 mL) and the resulting suspension was refluxed for 4-6 hour(s) (h). The excess $SOCl_2$ was removed under vacuum and toluene (20-30 mL) was added to the residue and again evaporated under vacuum to dryness. Chlorobenzene (10-20 mL) was added to the resulting residue under $N_2$ atmosphere folheated at 110° C. for 4-6 h. The reaction mixture was evaporated to dryness and extracted with EtOAc; the organic layer was washed with brine and dried over $Na_2SO_4$ and the solvent evaporated to dryness to afford 5a-c after silica gel column chromatography.

5a: $^1$H NMR (DMSO-d6) δ: 10.76 (s, 1H), 8.36-8.48 (m, 1H), 8.18-8.32 (m, 1H), 8.07-8.18 (m, 3H), 7.77-7.98 (m, 3H), 7.50-7.71 (m, 6H), 7.25-7.50 (m, 2H), 6.57 (d, J=15 Hz, 1H), 4.20 (q, J=7.2 Hz, 2H), 3.42 (br. s., 1H), 3.29 (br. s., 1H), 3.17 (s, 1H), 2.57 (br. s., 1H), 1.27 (t, J=7.0 Hz, 3H).

LC-ESMS m/z 422.40 [M+1]$^+$; HPLC; 99.58%; Yield=43.29%.

iv) (2E)-3-(3-{[(3-phenylnaphthalen-1-yl)carbonyl]amino}phenyl)prop-2-enoic acid (6a)

Method E: Compound 5a (1 equivalent) was dissolved in THF/$H_2O$ (1:1) mixture. LiOH.$H_2O$ (3 equivalents) was added to the reaction mixture and stirred at room temperature (rt) overnight. The reaction mixture was concentrated under vacuum to dryness. The resulting residue was adjusted to pH 5 with dilute HCl and the resulting suspension was stirred for some time following which the solid formed was filtered and washed with 50% ethyl acetate/petroleum ether mixture. The residue was dried under vacuum for 3 h to afford 6a as white solids.

6a: $^1$H NMR (DMSO-d6) δ: 10.74 (s, 1H), 8.41 (s, 1H), 8.22-8.28 (m, 1H), 8.07-8.14 (m, 3H), 7.83-7.94 (m, 3H), 7.41-7.65 (m, 8H), 6.47 (d, J=18 Hz, 1H).

LC-ESMS m/z 394.17[M+1]$^+$; HPLC; 99.2%; Yield=77.69%.

Example 2 (Compound 6b)

(2E)-3-(4-fluoro-3-{[(3-phenylnaphthalen-1-yl)carbonyl]amino}phenyl)prop-2-enoic acid i) Ethyl(2E)-3-(4-fluoro-3-{[(3-phenylnaphthalen-1-yl)carbonyl]amino}phenyl)prop-2-enoate (5b)

Compound 5b was synthesized from 2 (0.86 mmol) and ethyl(2E)-3-(3-amino-4-fluorophenyl)prop-2-enoate (4b) (0.71 mmol) using the procedure according to the above Method D.

5b: $^1$H NMR (DMSO-d6) δ: 10.55 (s, 1H), 8.41 (s, 1H), 8.29-8.35 (m, 1H), 8.08-8.21 (m, 3H), 7.92 (d, J=7.2 Hz, 2H), 7.53-7.73 (m, 6H), 7.36-7.48 (m, 2H), 6.63 (d, J=15 Hz, 1H), 4.20 (q, J=6.9 Hz, 2H), 1.26 (t, J=7.0 Hz, 3H)).

LC-ESMS m/z 437.87[M−1]$^−$; HPLC; 99.77%; Yield=32.44%.

ii) (2E)-3-(4-fluoro-3-{[(3-phenylnaphthalen-1-yl)carbonyl]amino}phenyl)prop-2-enoic acid (6b)

Compound 6b was synthesized from 5b (0.27 mmol) and LiOH.$H_2O$ (0.81 mmol) using the procedure according to the above Method E.

6b: $^1$H NMR (DMSO-d6) δ: 10.56 (s, 1H), 8.42 (s, 1H), 8.29-8.36 (m, 1H), 8.08-8.19 (m, 3H), 7.93 (d, J=7.6 Hz, 2H), 7.37-7.69 (m, 8H), 6.53 (d, J=15 Hz, 1H).

LC-ESMS m/z 410[M−1]$^−$; HPLC; 100%; Yield=53.40%.

Example 3 (Compound 6c)

(2E)-3-(4-chloro-3-{[(3-phenylnaphthalen-1-yl)carbonyl]amino}phenyl)prop-2-enoic acid i) Ethyl(2E)-3-(4-chloro-3-{[(3-phenylnaphthalen-1-yl)carbonyl]amino}phenyl)prop-2-enoate (5c)

Compound 5b was synthesized from 3 (0.86 mmol) and ethyl(2E)-3-(3-amino-4-chlorophenyl)prop-2-enoate (4c) (0.71 mmol) using the procedure according to the above Method D.

5c: LC-ESMS m/z 455.87[M+1]$^+$; HPLC; 100%; Yield=32.44%.

ii) (2E)-3-(4-chloro-3-{[(3-phenylnaphthalen-1-yl)carbonyl]amino}phenyl)prop-2-enoic acid (6c)

Compound 6c was synthesized from 5c (0.63 mmol) and LiOH.$H_2O$ (1.9 mmol) using the procedure according to the above Method E.

6c: $^1$H NMR (DMSO-d6) δ: 10.49 (s, 1H), 8.35-8.43 (m, 2H), 8.05-8.21 (m, 3H), 7.92 (d, J=7.6 Hz, 2H), 7.42-7.69 (m, 8H), 6.63 (d, J=15 Hz, 1H).

LC-ESMS m/z 425.80[M−1]$^−$; HPLC; 99.3%; Yield=55.84%.

The examples no.4 to 6 (corresponding to compounds no. 9a to 9c) according to this invention can be synthesized according to the procedure as depicted in reaction scheme 2.

Reaction Scheme 2:

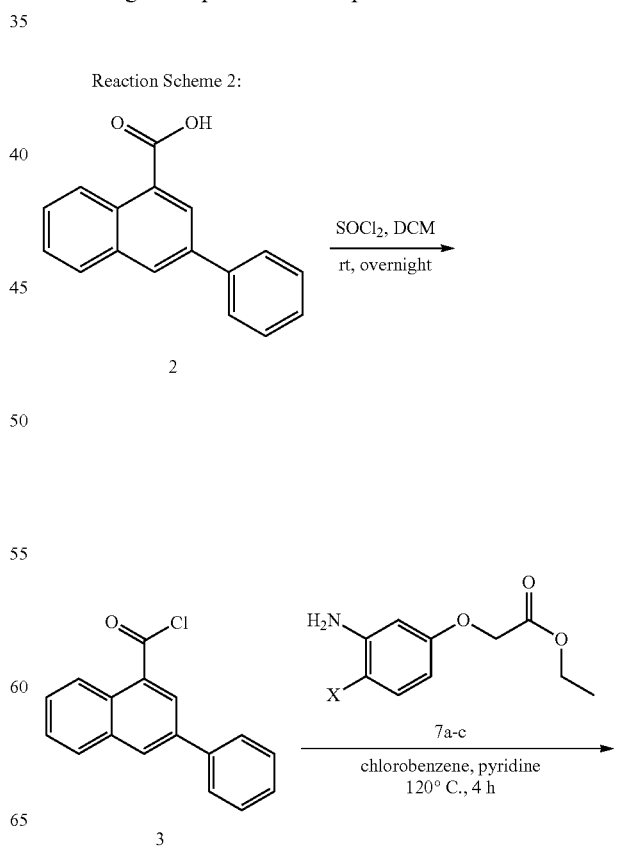

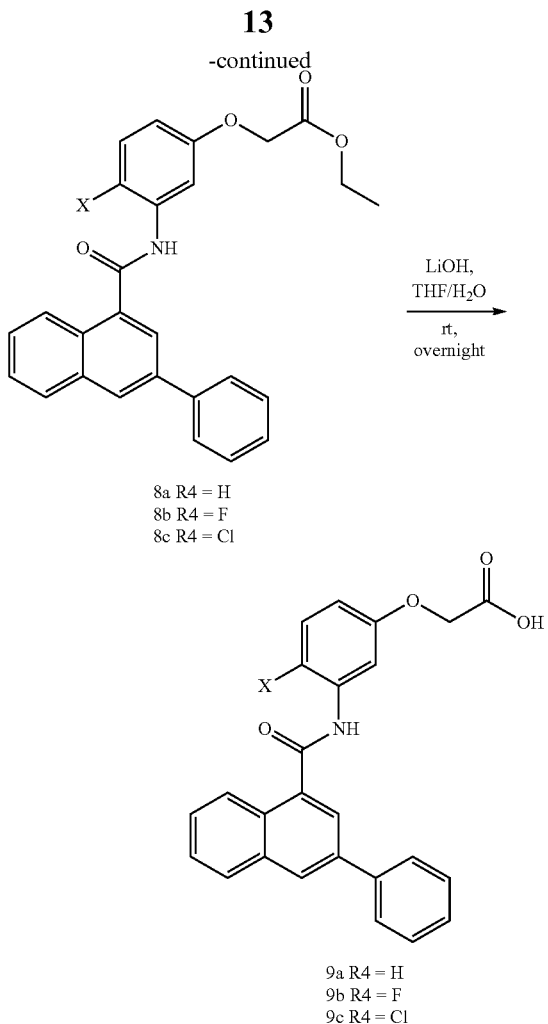

8a R4 = H
8b R4 = F
8c R4 = Cl

9a R4 = H
9b R4 = F
9c R4 = Cl

General Procedure for the Synthesis of Compounds 8a-c

Compound 2 (1 equivalent) was taken in $SOCl_2$ (10-20 mL) and the resulting suspension was refluxed for 4-7 h. The excess $SOCl_2$ was removed under vacuum and toluene (20-40 mL) was added to the residue and again evaporated under vacuum to dryness. Chlorobenzene (10-25 mL) was added to the resulting residue under $N_2$ atmosphere followed by addition of appropriate cinnaminate derivatives 7a-c (0.8-1.1 equivalents) and 0.5-1 mL pyridine. The reaction mixture was heated at 110-135° C. for 3-7 h. The reaction mixture was evaporated to dryness and extracted with EtOAc; the organic layer was washed with brine and dried over $Na_2SO_4$ and the solvent evaporated to dryness to afford 8a-c after silica gel column chromatography.

General Procedure for the Synthesis of Compounds 9a-c

Compound 8a-c (1 equivalent) was dissolved in $THF/H_2O$ (1:1) mixture. $LiOH.H_2O$ (3-5 equivalent) was added to the reaction mixture and stirred at room temperature overnight. At this point analysis by TLC indicated the starting material has been consumed. The reaction mixture was concentrated under vacuum to dryness. The resulting residue was adjusted to pH 4-5 with dilute HCl and the resulting suspension was stirred for some time following which the solid formed was filtered and washed with 50-70% ethyl acetate/petroleum ether mixture. The residue was dried under vacuum for 3-6 h to afford 9a-c as white solids.

Example 4 (Compound 9a)

3-{[(3-phenylnaphthalen-1-yl)carbonyl] amino}phenoxy)acetic acid i) Ethyl(3-{[(3-phenylnaphthalen-1-yl)carbonyl] amino}phenoxy)acetate (8a)

Compound 8a was synthesized from 3 (0.65 mmol) and ethyl(3-aminophenoxy)acetate (7a) (0.78 mmol) using the procedure according to the above Method D.
8a: LC-ESMS m/z 426.4 [M+1]$^+$; HPLC; 99%; Yield=29.36%.

ii)(3-{[(3-phenylnaphthalen-1-yl)carbonyl] amino}phenoxy)acetic acid (9a)

Compound 9a was synthesized from 8a (0.21 mmol) and $LiOH.H_2O$ (0.63 mmol) using the procedure according to the above Method E.
9a: $^1$H NMR (DMSO-d6) δ: 10.65 (s, 1H), 8.39 (s, 1H), 8.04-8.23 (m, 3H), 7.91 (d, J=7.2 Hz, 2H), 7.40-7.65 (m, 7H), 7.27 (t, J=8.3 Hz, 1H), 6.68 (dd, J=7.9, 2.3 Hz, 1H), 4.64 (s, 2H).
LC-ESMS m/z 396.4[M−1]−; HPLC; 100%; Yield=76.13%.

Example 5 (Compound 9b)

(4-fluoro-3-{[(3-phenylnaphthalen-1-yl)carbonyl] amino}phenoxy)acetic acid i) Ethyl(4-fluoro-3-{[(3-phenylnaphthalen-1-yl)carbonyl]amino}phenoxy)acetate (8b)

Compound 8b was synthesized from 3 (1.30 mmol) and ethyl(3-amino-4-fluorophenoxy) acetate (7b) (1.04 mmol) using the procedure according to the above Method D.
8b: LC-ESMS m/z 444.17 [M+1]$^+$; HPLC; 93%; Yield=48.12%.

ii) (4-fluoro-3-{[(3-phenylnaphthalen-1-yl)carbonyl] amino}phenoxy)acetic acid (9b)

Compound 9b was synthesized from 8b (0.60 mmol) and $LiOH.H_2O$ (1.80 mmol) using the procedure according to the Method E described above.
9b: $^1$H NMR (DMSO-d6) δ: 10.41 (br. s., 1H), 8.39 (s, 1H), 8.25-8.31 (m, 1H), 8.07-8.13 (m, 2H), 7.91 (d, J=7.6 Hz, 2H), 7.52-7.64 (m, 4H), 7.40-7.47 (m, 1H), 7.13-7.35 (m, 2H), 6.71 (dt, J=8.9, 3.7 Hz, 1H), 4.29 (s, 2H);
LC-ESMS m/z 414.17[M−1]−; HPLC; 99.40%; Yield=90.94%.

Example 6 (Compound 9c)

4-chloro-3-{[(3-phenylnaphthalen-1-yl)carbonyl] amino}phenoxy)acetic acid i) Ethyl(4-chloro-3-{[(3-phenylnaphthalen-1-yl)carbonyl]amino}phenoxy)acetate) (8c Compound 8c was synthesized from 3 (0.65 mmol) and ethyl(3-amino-4-chlorophenoxy)acetate (7c) (0.78 mmol) using the procedure according to the above Method D.
8c: LC-ESMS m/z 460.1 [M+1]$^+$; HPLC; 92%; Yield=43.08%.

ii) (4-chloro-3-{[(3-phenylnaphthalen-1-yl)carbonyl] amino}phenoxy)acetic acid (9c)

Compound 9c was synthesized from 8c (0.23 mmol) and LiOH.H$_2$O (0.71 mmol) using the procedure according to the Method E described above.

9c: $^1$H NMR (DMSO-d6) δ: 10.32 (s, 1H), 8.32-8.43 (m, 2H), 8.07-8.19 (m, 2H), 7.91 (d, J=7.2 Hz, 2H), 7.37-7.65 (m, 7H), 6.90 (dd, J=8.9, 2.8 Hz, 1H), 4.74 (s, 2H).

LC-ESMS m/z 430.25[M−1]$^-$; HPLC; 98.7%; Yield=80.34%.

The examples no. 7 and 8 (corresponding to compounds no. 11a and 11b) according to this invention can be synthesized according to the procedure as depicted in reaction scheme 3.

General Procedure for the Synthesis of Compounds 10a-b

Compound 5a-b (1 equivalent) was suspended in ethanol followed by addition of p-tolylsulfonyl hydrazide (3-7 equivalents) and NaOAc (9-15 equivalents). The reaction mixture was heated at 60-80° C. overnight. At this point analysis by LC-MS indicated the consumption of starting material and formation of the desired product. The reaction mixture was evaporated in vacuo to dryness and water was added to the residue and extracted with EtOAc and washed with water and brine. The organic layer was dried over Na$_2$SO$_4$, filtered, and the solvent was removed in vacuo. The resulting solid was purified using silica gel column chromatography using EtOAC/Petrol Ether as eluent.

Reaction Scheme 3:

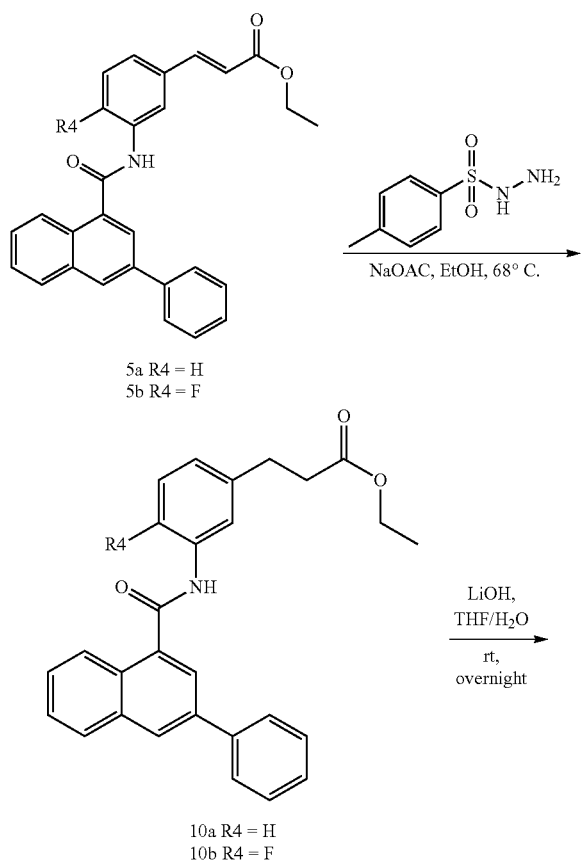

5a R4 = H
5b R4 = F

10a R4 = H
10b R4 = F

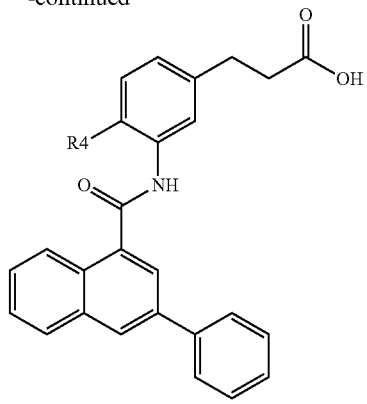

11a R4 = H
11b R4 = F

General Procedure for the Synthesis of Compounds 11a-b

Compound 10a-b (1 equivalent) was dissolved in THF/H$_2$O (1:1) mixture. LiOH.H$_2$O (3-6 equivalents) was added to the reaction mixture and stirred at room temperature overnight. At this point analysis by TLC indicated the starting material has been consumed. The reaction mixture was concentrated under vacuum to dryness. The resulting residue was adjusted to pH 4-5 with dilute HCl and the resulting suspension was stirred for some time following which the solid formed was filtered and washed with 50% ethyl acetate/petroleum ether mixture. The residue was dried under vacuum for 3-6 h to afford 11a-b as white solids.

Example 7 (Compound 11a)

3-(3-{[(3-phenylnaphthalen-1-yl)carbonyl] amino}phenyl) propanoic acid i) Ethyl 3-(3-{[(3-phenylnaphthalen-1-yl)carbonyl] amino}phenyl) propanoate (10a)

Method F:

Compound 5a (1 equivalent) was suspended in ethanol followed by addition of p-tolylsulfonyl hydrazide (3 equivalents) and NaOAc (9 equivalents). The reaction mixture was heated at 68° C. overnight. The reaction mixture was evaporated in vacuo to dryness and water was added to the residue and extracted with EtOAc and washed with water and brine. The organic layer was dried over Na$_2$SO$_4$, filtered, and the solvent was removed in vacuo. The resulting solid was purified using silica gel column chromatography using EtOAC/Petrol Ether as eluent.

$^1$H NMR (DMSO-d6) δ: 10.60 (s, 1H), 8.39 (s, 1H), 8.19-8.26 (m, 1H), 8.05-8.14 (m, 2H), 7.91 (d, J=7.2 Hz, 2H), 7.51-7.73 (m, 6H), 7.44 (d, J=7.2 Hz, 1H), 7.28 (t, J=7.7 Hz, 1H), 6.99 (d, J=7.6 Hz, 1H), 4.05 (q, J=7.2 Hz, 2H), 2.86 (t, J=7.4 Hz, 2H), 2.62 (t, J=7.6 Hz, 2H), 1.16 (t, J=7.0 Hz, 3H).

LC-ESMS m/z 424.17[M+1]$^+$; HPLC; 99.6%; Yield=90%.

ii) 3-(3-{[(3-phenylnaphthalen-1-yl)carbonyl] amino}phenyl) propanoic acid (11a)

Compound 11a was synthesized from 10a (1.41 mmol) and LiOH.H$_2$O (4.25 mmol) using the procedure according to the Method E described above.

11a: $^1$H NMR (DMSO-d6) δ: 12.17 (br. s., 1H), 10.61 (s, 1H), 8.40 (s, 1H), 8.20-8.27 (m, 1H), 8.03-8.14 (m, 2H), 7.92

(d, J=7.6 Hz, 2H), 7.41-7.73 (m, 7H), 7.29 (t, J=7.9 Hz, 1H), 7.01 (d, J=7.6 Hz, 1H), 2.61-2.89 (m, 4H).

LC-ESMS m/z 394.33[M−1]⁻; HPLC; 100%; Yield=66.35%.

Example 8 (Compound 11b)

3-(4-fluoro-3-{[(3-phenylnaphthalen-1-yl)carbonyl] amino}phenyl) propanoic acid i) Ethyl 3-(4-fluoro-3-{[(3-phenylnaphthalen-1-yl) carbonyl]amino}phenyl) propanoate (10b)

Compound 10b was synthesized from 5b (1.36 mmol), p-tolylsulfonyl hydrazide (839 mg, 4.50 mmol) and NaOAc (14.86 mmol) using the procedure according to the Method F described above.

$^1$H NMR (CHLOROFORM-d) δ: 8.36-8.41 (m, 1H), 8.18 (s, 1H), 7.93-8.04 (m, 3H), 7.74 (d, J=7.2 Hz, 2H), 7.49-7.62 (m, 4H), 7.27-7.45 (m, 1H), 6.95-7.09 (m, 2H), 4.17 (d, J=7.2 Hz, 1H), 4.17 (d, J=21.5 Hz, 1H), 3.01 (t, J=7.7 Hz, 2H), 2.69 (t, J=7.7 Hz, 2H), 1.27 (t, J=7.0 Hz, 3H).

LC-ESMS m/z 442.17[M+1]⁺; HPLC; 99.77%; Yield=56%.

ii) 3-(4-fluoro-3-{[(3-phenylnaphthalen-1-yl)carbonyl]amino}phenyl)propanoic acid (11 b)

Compound 11b was synthesized from 11a (1.36 mmol) and LiOH.H$_2$O (6.11 mmol) using the procedure according to the Method E described above.

11a: $^1$H NMR (DMSO-d6) δ: 10.42 (s, 1H), 8.41 (s, 1H), 8.29-8.33 (m, 1H), 8.09-8.14 (m, 2H), 7.93 (d, J=7.6 Hz, 2H), 7.53-7.68 (m, 5H), 7.42-7.48 (m, 1H), 7.12-7.26 (m, 2H), 2.81-2.88 (t, 2H), 1.99 (t, 2H).

LC-ESMS m/z 414.08[M+1]⁺; HPLC; 99.82; Yield=23.74%.

The examples no.9 to 15 (corresponding to compounds no. 17a to 17g) according to this invention can be synthesized according to the procedure as depicted in reaction scheme 5.

Reaction Scheme4:

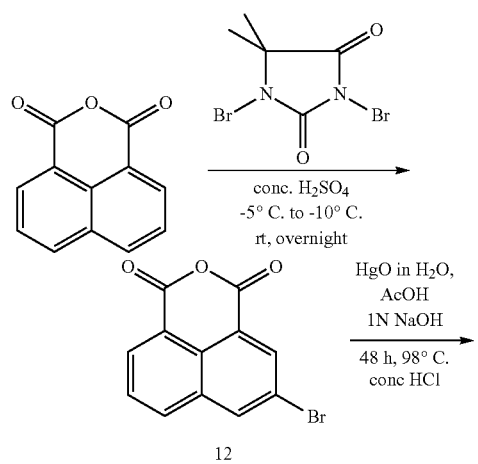

i) Preparation of 3-Bromonaphthallic Anhydride (12)

Method G:

To the naphthalic anhydride (0.5 mol), 0.5 L of 95-98% sulfuric acid was added at 20° C. The mixture was stirred at room temperature (rt) for 30 min. (minute(s)) to obtain complete dissolution and was cooled to −5 to −10° C. To the solution was added portionwise dibromodimethylhydantoin (0.27 mol) over 30 min while maintaining the internal reaction temperature between −10 to −5° C., and the mixture was stirred at this temperature for 1 h and allowed to warm slowly to room temperature overnight. The above reaction mixture was added to the 1 L of cold water with stirring over 30 min while maintaining the internal temperature below 75° C. The resulting slurry was cooled to 30° C. and filtered. The reaction flask was rinsed with 1 L of water, and the cake was washed with 500 mL of water and 500 mL of 10% water in N,N-Dimethylformamide (DMF). The wet cake was dried under vacuum overnight. To the crude product was added 1 L of DMF, and the slurry was warmed to 90° C. to give a homogeneous solution. The solution was allowed to cool to 70° C. and seeded with 1.00 g of pure 12. The slurry was allowed to cool to room temperature overnight. To the slurry was added 100 mL of water over 30 min, and the slurry was aged for 1 h and filtered. The wet cake was washed with 200 mL of 10% water in DMF and then with 200 mL of MeOH. The crude product was dried in vacuo at 70° C. for 3-4 h to give 12 as a creamish solid (yield=68%).

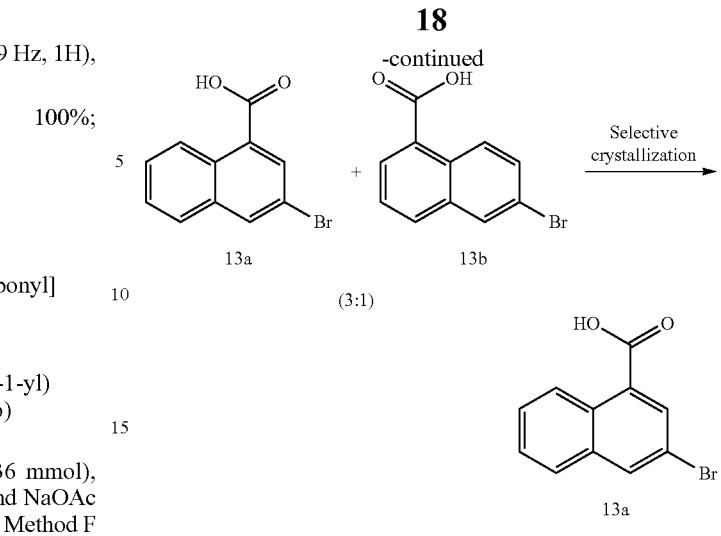

ii) Preparation of 3-Bromonaphthalic Acid (13a)

Method H:

To the 95 g of 12 (3-Bromonaphthallic Anhydride), 0.8 L of 1 N NaOH solution was added and resulting slurry was warmed to 60° C. A separate 500 mL round bottomed flask was charged with 78 g of solid yellow HgO, 228 mL of water, and 80 mL of AcOH, and the mixture was warmed to 50° C. to give a homogeneous, colorless solution. The freshly prepared mercury acetate solution was then added to the slurry of 12 in NaOH, and the reaction mixture was heated to 96-98° C. for 36 h. To the reaction mixture was then added 300 mL of concentrated HCl, and the mixture heated to 96-98° C. for 5 h, cooled to room temperature, and aged overnight at room temperature. The resulting solid was filtered, and the wet cake slurry was washed with water (3×350 mL) and then dried under vacuum to give 80 g of crude bromo acids 13a:13b (6-Bromonaphthalic acid) as a 1:3 mixture of regioisomers. In a 1-L round-bottomed flask were added 72 g of crude mixture of bromoacids 13a:13b and 0.6 L of AcOH, and the slurry was heated to reflux to give a homogeneous solution. The solution was allowed to slowly cool to 65° C., seeded with 1 g of pure 13a, allowed to slowly cool to room temperature, and aged overnight. The product was then collected by filtration, washed with heptane, and dried under vacuum for 3 h to give the desired regioisomeric product 13a as a colorless solid. ¹H NMR (DMSO-d6) δ: 8.79 (d, J=8.3 Hz, 1H), 8.46 (d, J=1.9 Hz, 1H), 8.15 (d, J=1.9 Hz, 1H), 7.97-8.06 (m, 1H), 7.60-7.72 (m, 2H).

LC-ESMS m/z 248.87 [M−1]⁻; HPLC purity: 100%; Yield=25%.

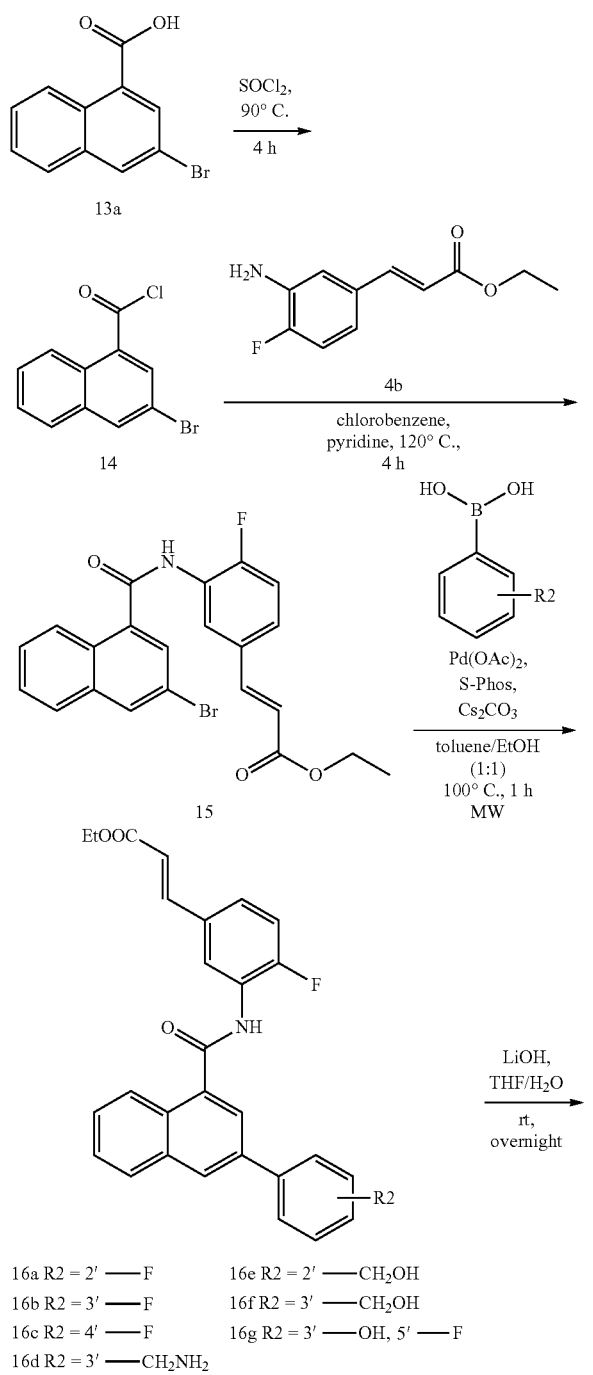

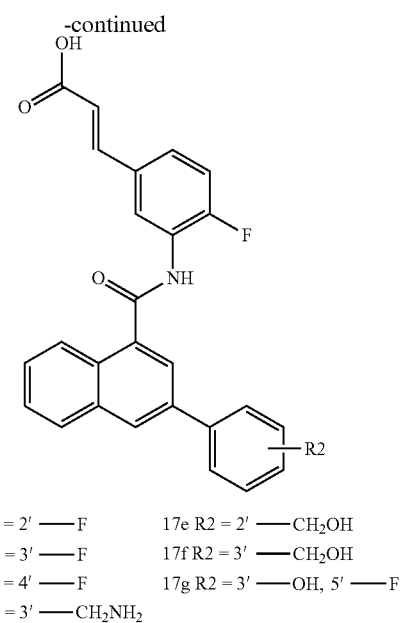

17a R2 = 2' ——F  17e R2 = 2' ——CH₂OH
17b R2 = 3' ——F  17f R2 = 3' ——CH₂OH
17c R2 = 4' ——F  17g R2 = 3' ——OH, 5' ——F
17d R2 = 3' ——CH₂NH₂

Preparation of Ethyl(2E)-3-(3-{[(3-bromonaphthalen-1-yl)carbonyl]amino}-4-fluoro-phenyl)prop-2-enoate (15)

Compound 13a (1 g, 3.98 mmol) was taken in SOCl₂ (20-30 mL) and the resulting suspension was refluxed for 4-6 h. The excess SOCl₂ was removed under vacuum and toluene (2×10 mL) was added to the residue and again evaporated under vacuum to dryness. Chlorobenzene (10-20 mL) was added to the resulting residue under N₂ atmosphere followed by addition of cinnaminate derivative 4b (618 mg, 3.18 mmol) and 0.9 mL pyridine. The reaction mixture was heated at 120-130° C. for 4-6 h. The reaction mixture was evaporated to dryness and extracted with EtOAc; the organic layer was washed with brine and dried over Na₂SO₄ and the solvent evaporated to dryness to afford crude 15. The crude material was suspended in methanol, sonicated and filtered to afford 792 mg (45%) pure 15 as a white solid.

¹H NMR (DMSO-d6) δ: 10.60 (s, 1H), 8.39-8.53 (m, 1H), 8.15-8.26 (m, 2H), 7.89-8.05 (m, 2H), 7.62-7.73 (m, 4H), 7.35-7.44 (m, 1H), 6.63 (d, J=18 Hz, 1H), 4.20 (q, J=7.2 Hz, 2H), 1.14-1.29 (t, 3H);

LC-ESMS m/z 442.00[M−1]⁻, HPLC purity-96.69%.

General Procedures for the Palladium-Catalyzed Synthesis of Ethyl(2E)-3-[4-fluoro-3-({[3-(substitutedphenyl)naphthalen-1-yl]carbonyl}amino)phenyl]prop-2-enoate 16a-g A Biotage Process Vial (5-20 mL) was charged with 4-7 mol % of S-Phos, 3-6 mol % of Pd(OAc)₂, compound 15 (1 equivalent), phenylboronic acid (1.5-2.5 equivalents), and Cs₂CO₃ (3-5 equivalents). The vial was charged with toluene/ethanol (1:1), stirred at room temperature for 10 min, and then irradiated at 100-130° C. for 1 h, using the microwave reactor Smith Synthesizer. After irradiation, the sample was cooled and the solvent was evaporated to dryness. The resulting residue was extracted with EtOAc; the organic layer was washed with brine and dried over Na₂SO₄ and the solvent evaporated to dryness to afford crude 16a-g. Purified material was obtained by silica gel column chromatography using EtOAc/Petrol ether as the eluent.

General Procedure for the Synthesis of Compounds 17a-g

Compound 16a-g (1 equivalent) was dissolved in THF/H₂O (1:1) mixture. LiOH.H₂O (2-6 equivalent) was added to the reaction mixture and stirred at room temperature overnight. At this point analysis by TLC indicated the starting material has been consumed. The reaction mixture was concentrated under vacuum to dryness. The resulting residue was adjusted to pH 4-5 with dilute HCl and the resulting suspension was stirred for some time following which the solid formed was filtered and washed with 50% ethyl acetate/petroleum ether mixture. The residue was dried under vacuum for 3-6 h to afford 17a-g as white solids.

Example 9 (Compound 17a)

(2E)-3-{3-[({3-[2-fluorophenyl]naphthalen-1-yl}carbonyl)amino]-4fluorophenyl}prop-2-enoic acid i) Ethyl(2E)-3-[4-fluoro-3-({[3-(2-fluorophenyl)naphthalen-1yl]carbonyl}amino)phenyl]prop-2-enoate (16a)

Method J:

To the mixture of 5 mol % of S-Phos, 5 mol % of Pd(OAc)₂, compound 15 (1 equivalent), 2-fluorophenylboronic acid (1.5 equivalents) and Cs₂CO₃ (3 equivalents) a mixture of toluene/ethanol (1:1) was added and stirred at room temperature for 10 min, and then irradiated at 110° C. for 1 h, using the microwave reactor. After irradiation, the sample was cooled and the solvent was evaporated to dryness. The resulting residue was extracted with EtOAc; the organic layer was washed with brine and dried over Na₂SO₄ and the solvent evaporated to dryness to afford crude 16a. Purified material was obtained by silica gel column chromatography using EtOAc/Petrol ether as the eluent.

¹H NMR (DMSO-d6) δ: 10.53 (s, 1H), 8.35 (s, 2H), 8.15 (m, 2H), 7.95 (s, 1H), 7.75 (m, 1H), 7.65 (m, 4H), 7.45 (m, 1H), 7.40 (m, 3H), 6.63 (d, J=15 Hz, 1H), 4.19 (q, J=6.9 Hz, 2H), 1.26 (t, J=6.9 Hz, 3H).

LC-ESMS m/z 458.32[M+1]⁺; HPLC purity-98.18%; Yield=45%.

ii) (2E)-3-{3-[({3-[2-fluorophenyl]naphthalen-1-yl}carbonyl)amino]-4fluorophenyl}prop-2-enoic acid (17a)

Compound 17a was synthesized from 16a (0.5 mmol) and LiOH.H₂O (5 mmol) using the procedure according to the Method E described above.

17a: ¹H NMR (DMSO-d6) δ: 10.53 (s, 1H), 8.30 (s, 2H), 8.15 (m, 2H), 7.95 (s, 1H), 7.75 (m, 1H), 7.65 (m, 4H), 7.45 (m, 1H), 7.40 (m, 3H), 6.53 (d, J=15 Hz, 1H).

LC-ESMS m/z 428.53 [M–1]⁻; HPLC purity-98%; Yield=37%.

Example 10 (Compound 17b)

(2E)-3-{3-[({3-[3-fluorophenyl]naphthalen-1-yl}carbonyl)amino]-4fluorophenyl}prop-2-enoic acid i) Ethyl(2E)-3-[4-fluoro-3-({[3-(3-fluorophenyl)naphthalen-1-yl]carbonyl}amino)phenyl]prop-2-enoate (16b)

Compound 16b was obtained by coupling 15 (0.57) with 3-fluorophenylboronic acid (0.85 mmol) using S-Phos (0.03 mmol), Pd(OAc)₂ (0.03 mmol) and Cs₂CO₃ (1.7 mmol) by using the procedure according to the above Method J.

¹H NMR (CHLOROFORM-d) δ: 8.86-8.92 (m, 1H), 8.36-8.42 (m, 1H), 8.18-8.20 (m, 1H), 7.96-8.05 (m, 3H), 7.42-7.75 (m, 5H), 7.27-7.35 (m, 1H), 7.09-7.21 (m, 2H), 6.50 (q, 2H), 4.29 (q, J=7.2 Hz, 2H), 1.24-1.39 (t, 3H).

LC-ESMS m/z 458.32[M+1]⁺; HPLC purity-94.03%; Yield=88.97%.

ii) (2E)-3-{3-[({3-[3-fluorophenyl]naphthalen-1-yl}carbonyl)amino]-4fluorophenyl}prop-2-enoic acid (17b)

Compound 17b was synthesized from 16b (0.5 mmol) and LiOH.H₂O (5 mmol) using the procedure according to the Method E described above.

17b: ¹H NMR (DMSO-d6) δ: 10.55 (s, 1H), 8.48 (s, 1H), 8.30-8.36 (m, 1H), 8.08-8.19 (m, 3H), 7.76-7.83 (m, 2H), 7.56-7.68 (m, 5H), 7.24-7.43 (m, 2H), 6.50 (d, 1H).

LC-ESMS m/z 428.53 [M–1]⁻; HPLC purity-94.09%; Yield=81%.

Example 11 (Compound 17c)

(2E)-3-{3-[({3-[4-fluorophenyl]naphthalen-1-yl}carbonyl)amino]-4fluorophenyl}prop-2-enoic acid i) Ethyl(2E)-3-[4-fluoro-3-({[3-(4-fluorophenyl)naphthalen-1-yl]carbonyl}amino)phenyl]prop-2-enoate (16c)

Compound 16c was obtained by coupling 15 (0.57 mmol) with 4-fluorophenyl boronic acid (0.85 mmol) using S-Phos (0.03 mmol), Pd(OAc)₂ (0.03 mmol) and Cs₂CO₃ (1.7 mmol) by using the procedure according to the Method J described above.

LC-ESMS m/z 458.32[M+1]⁺; Yield=88.97%.

ii) (2E)-3-{3-[({3-[4-fluorophenyl]naphthalen-1-yl}carbonyl)amino]-4fluorophenyl}prop-2-enoic acid (17c)

Compound 17c was synthesized from 16c (0.5 mmol) and LiOH.H₂O (5 mmol) using the procedure according to Method E described above.

17c: ¹H NMR (DMSO-d6) δ: 10.54 (br. s., 1H), 8.40 (br. s., 2H), 8.32 (br. s., 1H), 8.14 (br. s., 3H), 7.97 (br. s., 2H), 7.64 (br. s., 2H), 7.60 (br. s., 1H), 7.34-7.51 (m, 3H), 6.53 (d, J=18 Hz, 1H).

LC-ESMS m/z 439.50 [M–1]⁻; HPLC purity-92.10%; Yield=82%.

Example 12 (Compound 17d)

(2E)-3-{3[({3-[3-(aminomethyl)phenyl]naphthalen-1-yl}carbonyl)amino]-4fluorophenyl}prop-2-enoic acid i) Ethyl(2E)-3-{3[({3-[3-(aminomethyl)phenyl]naphthalen-1-yl}carbonyl)amino]-4-fluorophenyl}prop-2-enoate (16d)

Compound 16d was obtained by coupling 15 (1.58 mmol) with 3-aminomethylphenylboronic acid (2.37 mmol) using S-Phos (0.58 mmol), Pd(OAc)$_2$ (0.16 mmol) and Cs$_2$CO$_3$ (4.74 mmol) by using the procedure according to the Method J described above.

Yield=600 mg crude; this material was used directly for the next step without characterization.

ii) (2E)-3-{3[({3-[3-(aminomethyl)phenyl]naphthalen-1-yl}carbonyl)amino]-4-fluorophenyl}prop-2-enoic acid (17d)

Compound 17d was synthesized from 16d (1 g crude) and LiOH.H$_2$O (8.94 mmol) using the procedure according to Method E described above.

17d: $^1$H NMR (DMSO-d6) δ: 10.70 (br. s., 1H), 8.18-8.43 (m, 3H), 7.98-8.14 (m, 3H), 7.82 (d, J=7.9 Hz, 1H), 7.30-7.64 (m, 7H), 6.51 (d, J=18 Hz, 1H), 3.98 (br. s., 2H).

LC-ESMS m/z 439.50 [M−1]$^−$; HPLC purity-100%; Yield=27.86%.

Example 13 (Compound 17e)

(2E)-3-{4-fluoro-3-[({3-[2-(hydroxymethyl)phenyl]naphthalen-1-yl}carbonyl)amino]phenyl}prop-2-enoic acid i) Ethyl(2E)-3-{4-fluoro-3-[({3-[2-(hydroxymethyl)phenyl]naphthalen-1-yl}carbonyl)amino]phenyl}prop-2-enoate (16e)

Compound 16e was obtained by coupling 15 (1.1 mmol) with 2-hydroxymethyl phenylboronic acid (1.6 mmol) using S-Phos (0.11 mmol), Pd(OAc)$_2$ (0.05 mmol) and Cs$_2$CO$_3$ (2.2 mmol) by using the procedure according to the Method J described above.

$^1$H NMR (DMSO-d6) δ: 10.48 (s, 1H), 8.28-8.35 (m, 1H), 8.03-8.14 (m, 3H), 7.83 (s, 1H), 7.57-7.67 (m, 5H), 7.33-7.48 (m, 4H), 6.50 (d, J=18 Hz, 1H), 4.52 (br. s., 2H), 4.02 (q, 2H), 1.98 (s, 1H), 1.03-1.30 (t, 3H).

LC-ESMS m/z 468.20[M−1]$^−$; HPLC purity-99.34%; Yield=58%.

ii) (2E)-3-{4-fluoro-3-[({3-[2-(hydroxymethyl)phenyl]naphthalen-1-yl}carbonyl)amino]phenyl}prop-2-enoic acid (17e)

Compound 17e was synthesized from 16e (0.6 mmol) and LiOH.H$_2$O (1.8 mmol) using the procedure according to Method E described above.

17e: $^1$H NMR (DMSO-d6) δ: 10.58 (br. s., 1H), 8.23-8.46 (m, 2H), 8.14 (br. s., 3H), 7.73-7.92 (m, 2H), 7.36-7.72 (m, 7H), 6.53 (d, J=18 Hz, 1H), 4.63 (br. s., 2H), 1.98 (s, 1H).

LC-ESMS m/z 440.27 [M−1]$^−$; HPLC purity-98.47%; Yield=83%.

Example 14 (Compound 17f)

(2E)-3-{4-fluoro-3-[({3-[3-(hydroxymethyl)phenyl]naphthalen-1-yl}carbonyl)amino]phenyl}prop-2-enoic acid (17f)

i) Ethyl-3-{4-fluoro-3-[({3-[3-(hydroxymethyl)phenyl]naphthalen-1-yl}carbonyl)amino]phenyl}prop-2-enoate (16f)

Compound 16f was obtained by coupling 15 (700 mg, 1.58 mmol) with 3-hydroxymethylphenylboronic acid (1.74 mmol) using S-Phos (0.08 mmol), Pd(OAc)$_2$ (0.08 mmol) and Cs$_2$CO$_3$ (4.74 mmol) by using the procedure according to Method J described above.

LC-ESMS m/z 468.42[M−1]$^−$

Yield=58%; this material was used directly for the next step without characterization.

ii)(2E)-3-{4-fluoro-3-[({3-[3-(hydroxymethyl)phenyl]naphthalen-1-yl}carbonyl)amino]phenyl}prop-2-enoic acid (17f)

Compound 17f (27.86%) was synthesized from 16f (0.89 mmol) and LiOH.H$_2$O (8.94 mmol) using the procedure according to Method E described above.

17f: $^1$H NMR (DMSO-d6) δ: 12.43 (br. s., 1H), 10.56 (s, 1H), 8.40 (s, 1H), 8.27-8.34 (m, 1H), 8.09-8.19 (m, 3H), 7.86 (s, 1H), 7.78 (d, J=7.2 Hz, 1H), 7.58-7.70 (m, 3H), 7.51 (t, J=7.6 Hz, 1H), 7.35-7.44 (m, 2H), 6.55 (s, 1H), 6.50 (s, 1H), 5.31 (t, J=5.7 Hz, 1H), 4.62 (d, J=5.7 Hz, 2H).

LC-ESMS m/z 440.33[M−1]$^−$; HPLC purity-98.47%; Yield=27.86%.

Example 15 (Compound 17g)

(2E)-3-[4-fluoro-3-({[3-(3-fluoro-5-hydroxyphenyl)naphthalen-1yl]carbonyl}amino)phenyl]prop-2-enoic acid (17g)

i) Ethyl(2E)-3-[4-fluoro-3-({[3-(3-fluoro-5-hydroxyphenyl)naphthalen-1yl]carbonyl}amino)-phenyl]prop-2-enoate (16g)

Compound 16g was obtained by coupling 15 (1.14 mmol) with 3-fluoro5-hydroxyphenylboronic acid (1.71 mmol) using S-Phos (0.14 mmol), Pd(OAc)$_2$ (0.14 mmol) and Cs$_2$CO$_3$ (3.42 mmol) by using the procedure according to Method J described above.

$^1$H NMR (DMSO-d6) δ: 10.55 (s, 1H), 10.08-10.16 (m, 1H), 8.29-8.42 (m, 2H), 8.07-8.21 (m, 3H), 7.60-7.74 (m, 4H), 7.37-7.45 (m, 1H), 7.13-7.24 (m, 2H), 6.56-6.68 (m, 2H), 4.21 (q, J=7.2 Hz, 2H), 1.08-1.32 (t, J=7.2 Hz, 3H).

LC-ESMS m/z 474.56[M+1]$^+$; HPLC purity-99.88%; Yield=46%.

ii) (2E)-3-[4-fluoro-3-({[3-(3-fluoro-5-hydroxyphenyl)naphthalen-1yl]carbonyl}amino)phenyl]prop-2-enoic acid (17g)

Compound 17g was synthesized from 16g (0.42 mmol) and LiOH.H$_2$O (4.2 mmol) using the procedure according to Method E described above.

17g: $^1$H NMR (DMSO-d6) δ: 10.54 (s, 1H), 8.29-8.41 (m, 2H), 8.05-8.17 (m, 3H), 7.57-7.69 (m, 4H), 7.39 (t, J=9.3 Hz, 1H), 7.12-7.23 (m, 2H), 6.64 (t, J=2.1 Hz, 1H), 6.53 (d, J=15 Hz, 1H).

LC-ESMS m/z 444.62[M−1]$^−$; HPLC purity-99.88%; Yield=42%.

The example no.16 (corresponding to compound no. 18) according to this invention can be synthesized according to the procedure as depicted in reaction scheme 6.

Reaction Scheme 6:

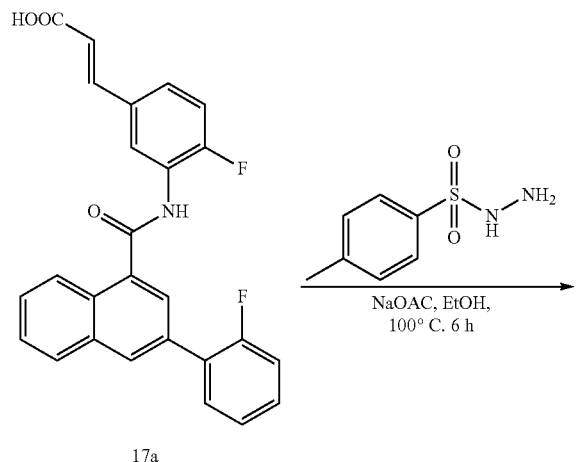

Example 16 (Compound 18)

3-[4-fluoro-3-({[3-(2-fluorophenyl)naphthalen-1yl]carbonyl}amino)phenyl]-propanoicacid Compound 18 was synthesized from 17a (0.58 mmol), p-tolylsulfonyl hydrazide (1.75 mmol) and NaOAc (5.25 mmol) using the procedure according to Method F described above.

$^1$H NMR (DMSO-d6) δ: 10.40 (s, 1H), 8.25-8.34 (m, 2H), 8.08-8.14 (m, 1H), 7.95 (s, 1H), 7.60-7.81 (m, 4H), 7.36-7.55 (m, 3H), 7.08-7.28 (m, 2H), 2.80-2.90 (t, 2H), 2.60 (t, 2H).

LC-ESMS m/z 430.20 [M−1]$^-$; HPLC purity-99.88%; Yield=39%.

The example no.17 (corresponding to compound no. 20) according to this invention can be synthesized according to the procedure as depicted in reaction scheme 7.

Reaction Scheme 7:

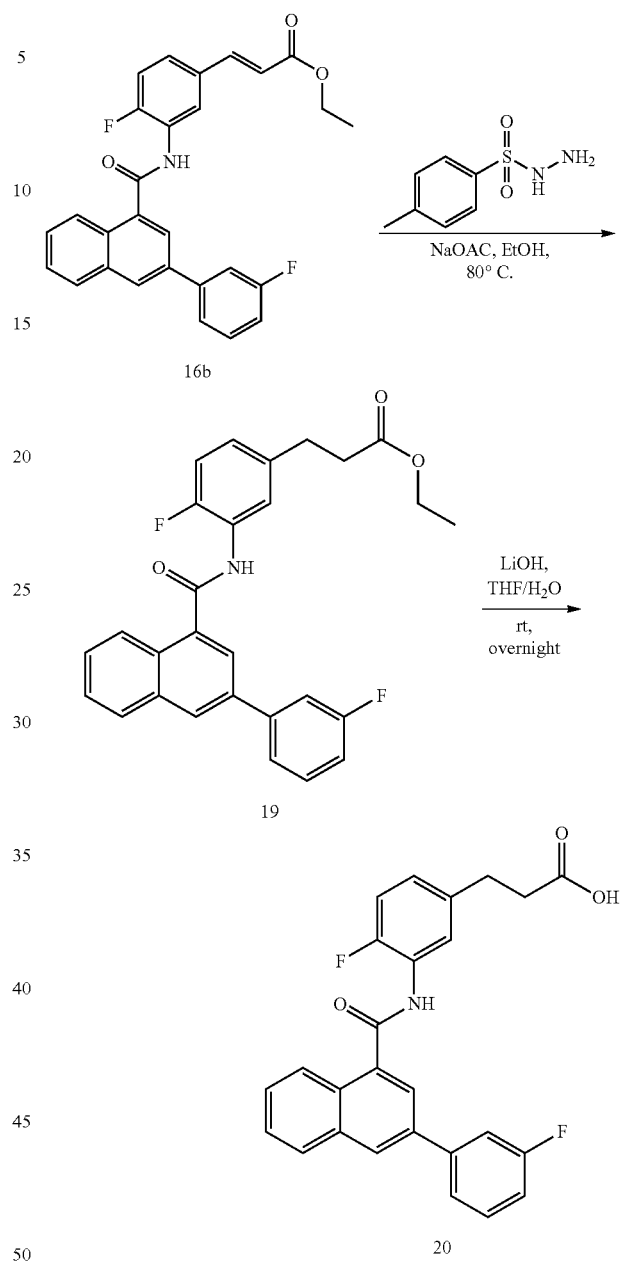

Example 17 (Compound 20)

3-[4-fluoro-3-({[3-(3-fluorophenyl)naphthalen-1-yl]carbonyl}amino)phenyl]propanoic acid i) Ethyl 3-[4-fluoro-3-({[3-(3-fluorophenyl)naphthalen-1-yl]carbonyl}amino)phenyl]propanoate (19)

Compound 19 was synthesized from 16b (4.37 mmol), p-tolylsulfonyl hydrazide (13.1 mmol) and NaOAc (39.3 mmol) using the procedure according to Method F described above.

LC-ESMS m/z 458.25[M−1]$^-$; HPLC purity-85.73%.

Yield=80%; this material was directly used for the next step without purification.

ii) 3-[4-fluoro-3-({[3-(3-fluorophenyl)naphthalen-1-yl]carbonyl}amino)phenyl]propanoic acid (20)

Compound 20 was synthesized from 19 (3.26 mmol) and LiOH.H$_2$O (32.6 mmol) using the procedure according to Method E described above.

$^1$H NMR (DMSO-d6) δ: 10.38 (br. s., 1H), 8.46 (s, 1H), 8.28-8.34 (m, 1H), 8.07-8.16 (m, 2H), 7.74-7.83 (m, 2H), 7.55-7.69 (m, 4H), 7.21-7.30 (m, 2H), 7.11-7.20 (m, 1H), 2.78-2.88 (t, 2H), 2.72 (d, J=1.9 Hz, 1H), 2.52-2.56 (m, 1H).

LC-ESMS m/z 430.20 [M–1]$^-$; HPLC 99.1%; Yield=41.57%.

The example no.18 (corresponding to compound no. 22) according to this invention can be synthesized according to the procedure as depicted in reaction scheme 8.

Reaction Scheme 8:

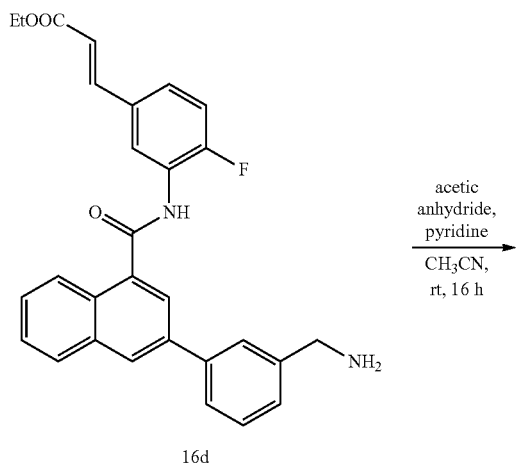

16d

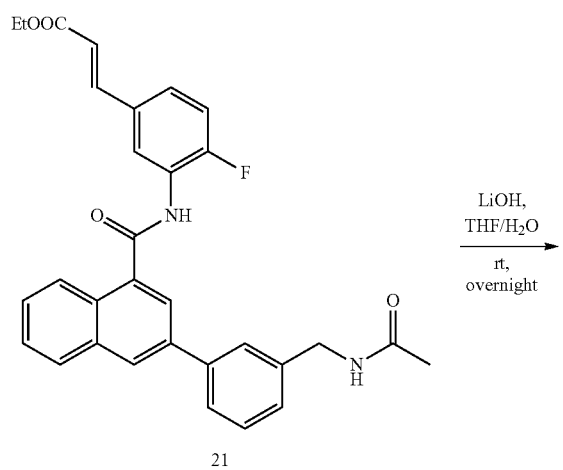

21

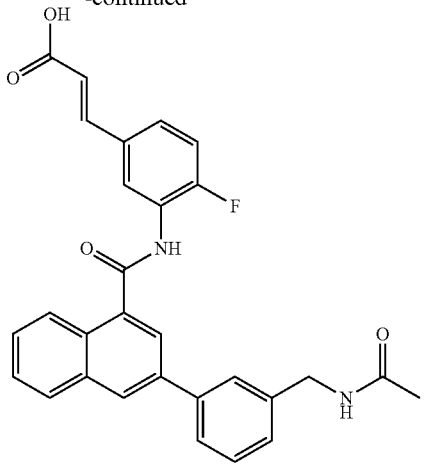

22

Example 18 (Compound 22)

2E)-3-(3-{[(3-{3-[(acetylamino)methyl]phenyl}naphthalen-1-yl)carbonyl]amino}-4 fluorophenyl)prop-2-enoic acid (22)

Compound 16d (600 mg crude) was dissolved in acetonitrile (15 mL), acetic anhydride (1 mL) and pyridine (1 mL) were added to the reaction mixture and stirred at rt for 16 h. The reaction mixture was evaporated to dryness. To the crude was added THF/water (1:1, 50 mL) followed by lithium hydroxide 1.5 g and the reaction was stirred at rt for 16 h. The reaction mixture was concentrated under vacuum to dryness. The resulting residue was adjusted to pH 5 with dilute HCl and the resulting suspension was stirred for some time following which the solid formed was filtered, dried under vacuum and purified by reverse phase HPLC.

$^1$H NMR (DMSO-d6) δ: 10.57 (s, 1H), 8.27-8.48 (m, 3H), 8.03-8.14 (m, 3H), 7.75-7.81 (m, 2H), 7.30-7.64 (m, 7H), 6.50 (d, J=18 Hz, 1H), 4.37 (d, J=6 Hz, 1H), 1.89 (s, 3H).

LC-ESMS m/z 481.60 [M–H]$^-$; HPLC 95.2%.

The example no.19 and 20 (corresponding to compound no. 25a and 25b) according to this invention can be synthesized according to the procedure as depicted in reaction scheme 9.

Example 19 (Compound 25a)

(2E)-3-[3-({[3-(3-hydroxyphenyl)naphthalen-1-yl]carbonyl}amino)phenyl]prop-2-enoic acid i) Ethyl(2E)-3-(3-{[(3-bromonaphthalen-1-yl)carbonyl]amino}-phenyl)prop-2-enoate (23)

Compound 13a (3.98 mmol) was taken in SOCl$_2$ (15 mL) and the resulting suspension was refluxed for 4 h. The excess SOCl$_2$ was removed under vacuum and toluene (2×10 mL) was added to the residue and again evaporated under vacuum to dryness. Chlorobenzene (15 mL) was added to the resulting residue under N$_2$ atmosphere followed by addition of ethyl (2E)-3-(3-aminophenyl)prop-2-enoate (3.9 mmol) and 1.0 mL pyridine. The reaction mixture was heated at 120° C. for 4 h. The reaction mixture was evaporated to dryness and extracted with EtOAc; the organic layer was washed with brine and dried over $Na_2SO_4$ and the solvent evaporated to dryness to afford crude 23. The crude material was suspended in methanol, sonicated and filtered to afford pure 23 as a white solid.

MS; m/z 426.00[M+1]$^+$; Yield=47%.

ii) Ethyl(2E)-3-[3-({[3-(3-hydroxyphenyl)naphthalen-1-yl]carbonyl}amino)phenyl]prop-2-enoate (24a)

Compound 24a was obtained by coupling 23 (1.88 mmol) with 3-hydroxyphenylboronic acid (2.82 mmol) using S-Phos (0.094 mmol), Pd(OAc)$_2$ (0.094 mmol) and Cs$_2$CO$_3$ (5.64 mmol) using procedure according to the Method J described above.

$^1$H NMR (DMSO-d6) δ: 10.74 (s, 1H), 9.61 (s, 1H), 8.34 (s, 1H), 8.21-8.27 (m, 1H), 8.08-8.15 (m, 2H), 8.02 (d, J=1.5 Hz, 1H), 7.84 (d, J=7.9 Hz, 1H), 7.42-7.68 (m, 4H), 7.25-7.36 (m, 3H), 6.81-6.87 (m, 1H), 6.59 (s, 1H), 6.54 (s, 1H), 4.19 (q, J=7.2 Hz, 2H), 1.07-1.30 (t, 3H).

LC-ESMS m/z 438.17 [M+H]$^+$; HPLC 97.7%; Yield=67%.

Reaction Scheme 9:

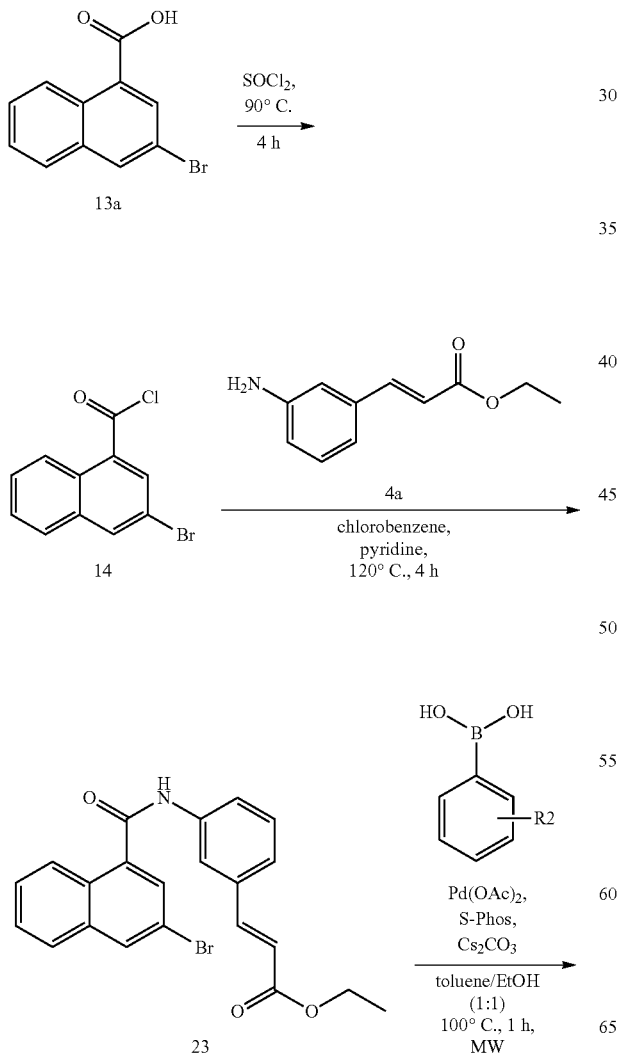

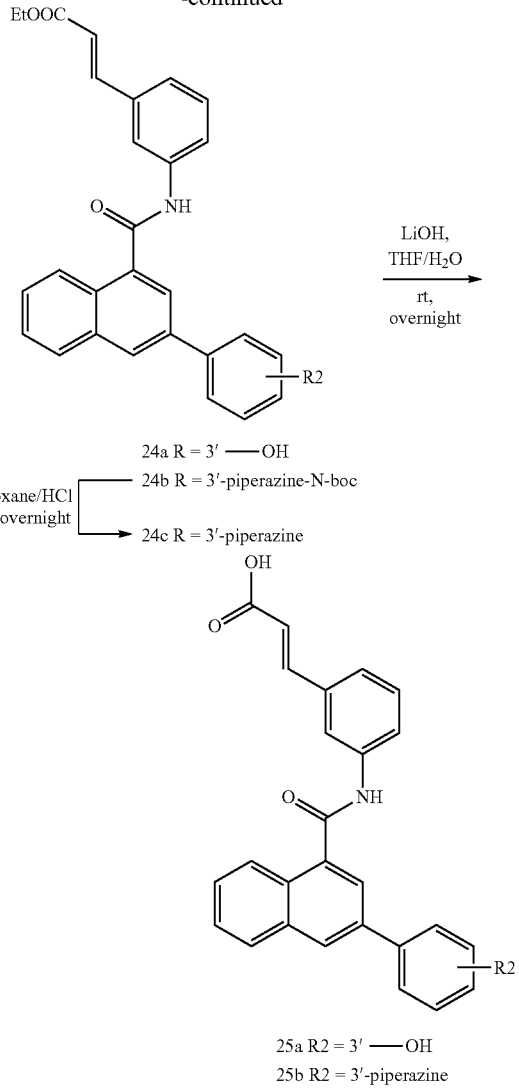

iii) (2E)-3-[3-({[3-(3-hydroxyphenyl)naphthalen-1-yl]carbonyl}amino)phenyl]prop-2-enoic acid (25a)

Compound 25a was synthesized from 24a (1.02 mmol) and LiOH.H$_2$O (10.3 mmol) using procedure according to the Method E described above.

$^1$H NMR (DMSO-d6) δ: 12.46 (br. s., 1H), 10.74 (s, 1H), 9.61 (s, 1H), 8.20-8.37 (m, 2H), 8.03 (s, 1H), 8.11 (s, 2H), 7.85 (d, J=7.2 Hz, 1H), 7.54-7.64 (m, 3H), 7.40-7.50 (m, 2H), 7.23-7.37 (m, 3H), 6.83 (d, J=3.4 Hz, 1H), 6.47 (d, J=15 Hz, 1H).

LC-ESMS m/z 408.33 [M–H]$^-$, HPLC 97.32%, yield=44%.

Example 20 (Compound 25b)

(2E)-3-{3[({3-[3-(piperazin-1-yl)phenyl]naphthalen-1-yl}carbonyl)amino]phenyl}prop-2-enoic acid i) Tert-butyl 4-{3-[4-({3-[(1E)-3-ethoxy-3-oxoprop-1-en-1-yl]phenyl}carbamoyl)naphthalen-2-yl]phenyl}piperazine-1-carboxylate (24b)

Compound 24b (302 mg, 53%) was obtained by coupling 23 (400 mg, 0.92 mmol) with {3-[4-(tert-butoxycarbonyl)

piperazin-1-yl]phenyl}boronic ester (439.3 mg, 1.13 mmol) using S-Phos (15.0 mg, 0.036 mmol), Pd(OAc)$_2$ (4.1 mg, 0.018 mmol) and Cs2CO3 (601 mg, 1.84 mmol) using the general procedure described above for 16a-g. This material was used directly for the next step.

LC-ESMS m/z 606.08[M+1]$^+$; HPLC; 95.7%; Yield=53%.

ii) Ethyl(2E)-3-{3[({3-[3-(piperazin-1-yl)phenyl]naphthalen-1-yl}carbonyl)amino]phenyl}prop-2-enoate (24c)

To 24 b (292 mg, 0.48 mmol) added HCl/dioxane solution (20 mL) and the reaction mixture was stirred at room temperature overnight. The volatiles were removed in vacuo, dried followed by addition of NaHCO$_3$ and extracted with 5% EtOAC/MeOH (3×20 mL) solution. The organic layer was dried over Na$_2$SO$_4$, filtered, and the solvent was removed in vacuo. The resulting solid was purified using silica gel column chromatography using 2% MeOH in dichloromethane (DCM) as eluent to afford 24c as a white solid.

$^1$H NMR (DMSO-d6) δ: 10.73 (s, 1H), 8.39 (s, 1H), 8.07-8.26 (m, 4H), 7.84 (d, J=7.6 Hz, 1H), 7.67 (s, 1H), 7.28-7.63 (m, 8H), 6.99 (d, J=8.3 Hz, 1H), 6.56 (d, J=18 Hz, 1H), 4.19 (q, J=7.2 Hz, 2H), 3.12-3.27 (m, 4H), 2.82-2.93 (m, 4H), 1.04-1.29 (m, 3H);

LC-ESMS m/z 505.62[M+1]$^+$; HPLC=96.8%; Yield=77.14%.

iii) (2E)-3-{3[({3-[3-(piperazin-1-yl)phenyl]naphthalen-1-yl}carbonyl)amino]phenyl}prop-2-enoic acid (25b)

Compound 25b (107 mg, 75%) was synthesized from 24c (150 mg, 0.3 mmol) and LiOH.H$_2$O (38 mg, 0.89 mmol) using procedure according to the Method E described above.

$^1$H NMR (DMSO-d6) δ: 10.66 (br. s., 1H), 8.32 (br. s., 1H), 8.02 (br. s., 4H), 7.78 (br. s., 1H), 7.22-7.57 (m, 9H), 6.94 (br. s., 1H), 6.38 (d, J=18 Hz, 1H), 3.18 (br. s., 4H), 2.90 (br. s., 4H);

LC-ESMS m/z 476.25[M−1]$^-$; HPLC; 98.5%, yield=75%.

The example no. 21 and 22 (corresponding to compound no. 28 and 29) according to this invention can be synthesized according to the procedure as depicted in reaction scheme 10.

General Procedure for the Synthesis of Compounds 28 and 29:

A Biotage Process Vial (5-20 mL) was charged with 4-7 mol % of (2,2'-Bis(diphenylphosphino)-1,1'-binaphthyl) BINAP, 1-2 mol % of Pd$_2$(dba)$_3$, compound 15 or 23 (1 equivalent), morpholine or piperidine (2-5 equivalents), and potassium tertbutoxide (2-4 equivalents). The vial was charged with DMF (5-10 mL) and irradiated at 100-130° C. for 1 h, using the microwave reactor Smith Synthesizer. After irradiation, the sample was cooled and diluted with water and extracted with ethyl acetate (3×50 mL). The organic layer was washed with water, brine and dried over Na$_2$SO$_4$ and the solvent evaporated to dryness to afford crude 28 or 29. Purified material was obtained by preparative HPLC.

Reaction Scheme 10

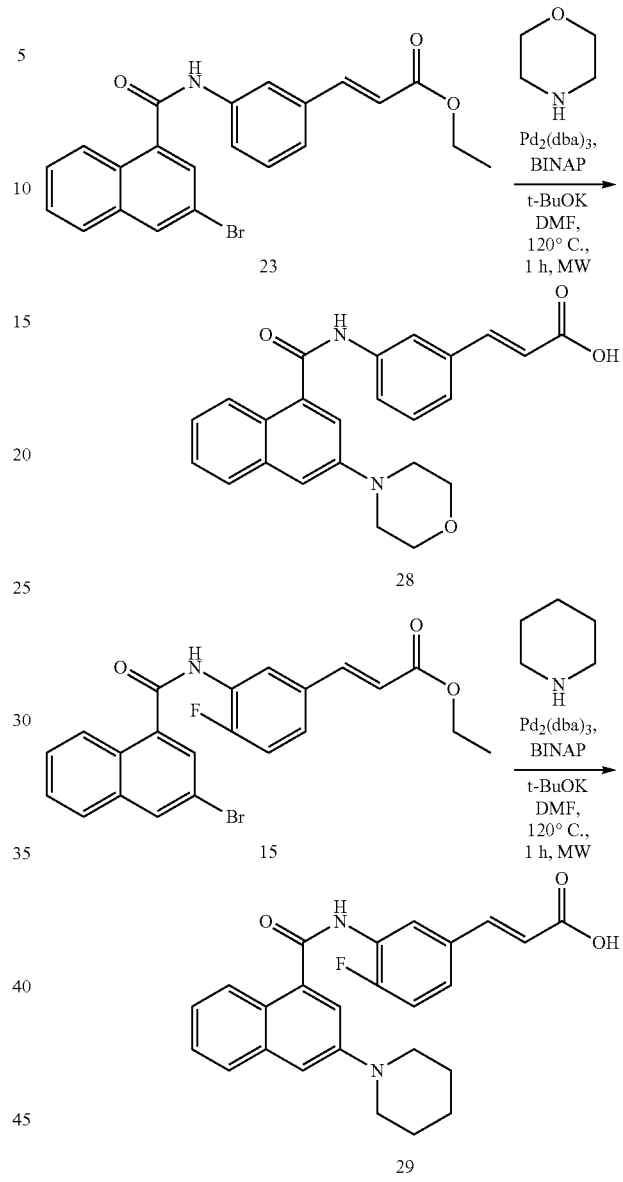

Example 21 (Compound 28)

(2E)-3-[3-({[3-(morpholin-4-yl)naphthalen-1-yl]carbonyl}amino)phenyl]prop-2-enoic acid A Biotage Process Vial (5-20 mL) was charged with (BINAP) (0.47 mmol), Pd$_2$(dba)$_3$ (0.11 mmol), ethyl(E)-3-[3-[(3-bromonaphthalene-1-carbonyl)amino]phenyl]prop-2-enoate (23) (1.17 mmol), morpholine (3.53 mmol), and potassium tertbutoxide (2.35 mmol). The vial was charged with DMF (5 mL) and irradiated at 100-130° C. for 1 h, using the microwave reactor Smith Synthesizer. After irradiation, the sample was cooled and diluted with water and extracted with ethyl acetate (3×50 mL). The organic layer was washed with water, brine and dried over Na$_2$SO$_4$ and the solvent evaporated to dryness to afford crude 28, which was purified by preparative HPLC.

$^1$H NMR (DMSO-d6) δ: 8.01 (d, J=5.3 Hz, 1H), 7.98 (s, 1H), 7.81 (d, J=7.9 Hz, 2H), 7.58 (d, J=2.6 Hz, 1H), 7.54 (s, 1H), 7.49 (s, 1H), 7.40-7.45 (m, 2H), 7.32-7.35 (m, 2H), 6.44 (d, J=15 HZ, 1H), 3.76-3.80 (m, 4H), 3.25-3.29 (m, 4H); MS; m/z 401.27[M−1]$^−$; HPLC purity-98.30%; Yield=16%.

Example 22 (Compound 29)

(2E)-3-[4-fluoro-3-({[3-(piperidin-1-yl) naphthalen-1-yl]carbonyl}amino)phenyl]prop-2-enoic acid A Biotage Process Vial (5-20 mL) was charged with BINAP (0.36 mmol), Pd$_2$(dba)$_3$ (0.18 mmol), ethyl(E)-3-[3-[(3-bromonaphthalene-1-carbonyl)amino]-4-fluoro-phenyl] prop-2-enoate (15) (1.81 mmol), piperidine (5.44 mmol), and potassium tertbutoxide (3.62 mmol). The vial was charged with DMF (5 mL) and irradiated at 100-130° C. for 1 h, using the microwave reactor Smith Synthesizer. After irradiation, the sample was cooled and diluted with water and extracted with ethyl acetate (3×50 mL). The organic layer was washed with water, brine and dried over Na$_2$SO$_4$ and the solvent evaporated to dryness to afford crude 29, which was purified by preparative HPLC.

$^1$H NMR (DMSO-d6) δ: 10.33 (s, 1H), 8.01 (d, J=8.3 Hz, 2H), 7.73 (d, J=7.9 Hz, 1H), 7.52-7.60 (m, 3H), 7.15-7.40 (m, 4H), 6.45 (d, J=18 Hz, 1H), 2.47 (s, 2H), 2.37 (d, J=1.9 Hz, 1H), 1.56-1.75 (m, 5H), 1.50 (br. s., 2H); MS; m/z 417.33[M−1]$^−$; HPLC purity- 100%; Yield=5%.

The example no.23 (corresponding to compound no. 27) according to this invention can be synthesized according to the procedure as depicted in reaction scheme 11.

Example 23 (Compound 27)

(2E)-3-(3-{[(3-{3-[(dimethylcarbamoyl)oxy]phenyl}naphthalen-1-yl)carbonyl]amino}phenyl)prop-2-enoic acid i) Ethyl(2E)-3-(3-{[(3-{3-[(dimethylcarbamoyl)oxy]phenyl}naphthalen-1-yl) carbonyl]amino}phenyl)prop-2-enoate (26)

To a flask containing 24a (0.9 mmol, 1.0 equivalent) in 10 mL of anhydrous CH$_2$Cl$_2$ was added NEt$_3$ (4.57 mmol, 5.0 equivalents). 4-nitrophenyl chloroformate (1.37 mmol, 1.5 equivalents) was added slowly to the reaction flask at 0° C., and the solution was stirred until the reaction was complete (3 h) as determined by TLC. N,N-dimethylamine hydrochloride (2.74 mmol, 3 equivalents) was added and the reaction mixture was stirred at room temperature for 2 h. The solution was then diluted with DCM, and washed with water, aqueous K$_2$CO$_3$ solution and brine. The organic layer was dried over Na$_2$SO$_4$, filtered, and the solvent was removed in vacuo. The resulting solid was purified using silica gel column chromatography using EtOAc/Pet Ether as eluent to afford 26 as a white solid.

$^1$H NMR (CHLOROFORM-d) δ: 8.30-8.35 (m, 1H), 8.22 (s, 1H), 8.09 (s, 1H), 7.89-7.95 (m, 3H), 7.67-7.75 (m, 1H), 7.29-7.63 (m, 8H), 7.07-7.25 (m, 1H), 6.48 (d, J=18, Hz 1H), 4.24 (d, J=7.2 Hz, 2H), 3.11 (s, 3H), 2.98 (s, 3H), 1.33 (t, J=7.0 Hz, 3H).

LC-ESMS m/z 509.00 [M+1]; HPLC purity-99.91%; Yield=36%.

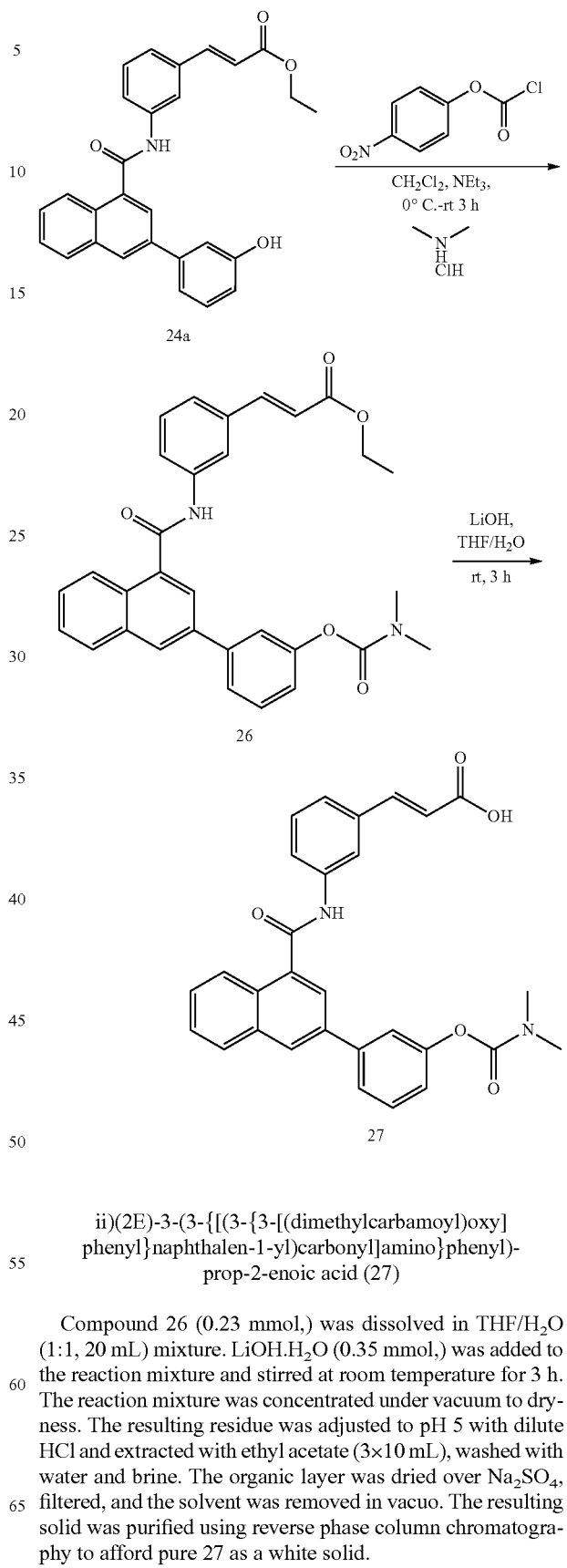

Reaction Scheme 11:

ii)(2E)-3-(3-{[(3-{3-[(dimethylcarbamoyl)oxy]phenyl}naphthalen-1-yl)carbonyl]amino}phenyl)-prop-2-enoic acid (27)

Compound 26 (0.23 mmol,) was dissolved in THF/H$_2$O (1:1, 20 mL) mixture. LiOH.H$_2$O (0.35 mmol,) was added to the reaction mixture and stirred at room temperature for 3 h. The reaction mixture was concentrated under vacuum to dryness. The resulting residue was adjusted to pH 5 with dilute HCl and extracted with ethyl acetate (3×10 mL), washed with water and brine. The organic layer was dried over Na$_2$SO$_4$, filtered, and the solvent was removed in vacuo. The resulting solid was purified using reverse phase column chromatography to afford pure 27 as a white solid.

$^1$H NMR (DMSO-d6) δ: 10.76 (s, 1H), 8.46 (s, 1H), 8.23-8.29 (m, 1H), 8.07-8.16 (m, 3H), 7.78-7.88 (m, 2H), 7.41-7.72 (m, 8H), 7.16-7.22 (m, 1H), 6.44 (d, J=15, Hz 1H), 3.09 (s, 3H), 2.93 (s, 3H).

LC-ESMS m/z 479.04[M−1]$^-$; HPLC purity-97.51%; Yield=66%.

Commercial Utility

The compounds of the invention have—as EP2 agonists—valuable pharmaceutical properties which make them commercially utilizable. EP2 agonists are thought to be useful in the treatment or prophylaxis of a variety of diseases and disorders.

The compounds of the invention activate the EP2 receptor activity on cells that express the EP2 receptor including mast cells, macrophages, endothelial cells, smooth muscle cells, fibroblasts, osteoblasts, epithelial cells and various leucocytes such as neutrophils, eosinophils, basophils, monocytes, dendritic cells, lymphocytes and natural killer cells. EP2 agonists are described to inhibit eosinophil degranulation, neutrophilic oxidative burst, differentiation of T cells into Th2 cells, cytokine and TNFalpha release of monocytes and macrophages, leukotriene release of leukocytes and infiltration of leukocytes into inflamed tissue (Takahashi et al. 2009, J. Pharmacol. Exp. Ther. 331, 656-670; reviewed by C. Vancheri et al. 2004, Trends Immunol. 25: 40-46). Moreover, EP2 agonists are known to inhibit the proliferation of fibroblasts and TGF-β induced myofibroblast transition (White et al. 2008, J. Immunol. 180: 637-646; Kolodsick et al. 2003, Am. J. Resp. Cell Mol. Biol. 29: 537-544). In addition, EP2 agonists are known to induce bronchodilation (Gauvreau et al. 1999, Am. J. Respir. Crit. Care Med. 159: 31-36; Forselles et al. 2011, Br. J. Pharmacol. 164: 1847-1856; Buckley et al. 2011, Thorax 66: 1029-1035). Further actions of EP2 agonists are described in kidney, eye, bone and gastrointestinal tract.

Correspondingly, the invention further relates to the compounds of the invention for use in the treatment or prophylaxis of diseases, especially diseases being alleviated by agonism of an EP2 receptor, in particular the diseases exemplified below.

The compounds of the invention are distinguished by one or more valuable and desirable properties, such as, for example, high efficacy, high selectivity, low toxicity, superior bioavailability in general (e.g. good enteral absorption), superior therapeutic window, superior pharmacokinetics (e.g. half-life), absence of significant side effects, and further beneficial effects related with their therapeutic and pharmaceutical suitability.

Accordingly, the invention further relates to compounds for use in the treatment or prophylaxis of human diseases, disorders or symptoms. In particular, the invention relates to the compounds of the invention for use in the treatment or prophylaxis of the following diseases:

Acute or chronic airway diseases, including bronchial asthma, chronic asthmatic disorders with reduced lung function and airway hyperreactivity, bronchial acute exacerbations, chronic bronchitis, acute respiratory distress syndrome, chronic obstructive pulmonary disorder (COPD), pulmonary artery hypertention (PAH) and pulmonary fibrosis, cystic fibrosis;

Inflammatory or allergic diseases, including allergic or chronic rhinitis and nasal polyposis;

Skin diseases associated with inflammatory or allergic disorders, including pruritus, atopic dermatitis, eczema, psoriasis, dermatitis, erythema multiforma, scleroderma, hypersensitivity vasculitis, hypersensitivity angiitis, urticaria, bullous pemphigoid, lupus erythematosus and pemphigus, pemphigus vulgaris and Hyper IgE syndrome;

Eye diseases associated with inflammatory or allergic disorders, including conjunctivitis;

Eye diseases associated with non-inflammatory disorders, including glaucoma;

Intestinal diseases associated with inflammatory or allergic disorders, including inflammatory bowel disease, constipation-predominant irritable bowel syndrome, Crohn's disease, eosinophil-related disorders including eosinophilic esophagitis, eosinophilic gastroenteritis and eosinophilic pancreatitis;

Systemic eosinophilic diseases including hypereosinophilia and Churg-Strauss-Syndrome;

Diseases which are based on an excessive release of TNF and leukotrienes, such as, for example, diseases of the arthritis type like rheumatoid arthritis, rheumatoid spondylitis, osteoarthritis and other arthritic conditions;

Diseases with ongoing fibrosis such as, but not limited to, cystic fibrosis, pulmonary fibrosis, hepatic fibrosis, renal fibrosis, myelofibrosis, retroperitoneal fibrosis, endomyocardial fibrosis, mediastinal fibrosis, nephrogenic systemic fibrosis, hypertrophic scars or toxic liver damage;

Bone disorders including osteoporosis and bone fracture;

Kidney disorders including acute and chronic kidney failure;

Transplant rejection including rejection of cardiac allograft, skin allograft, lung transplants, liver transplant, corneal allograft, renal allograft and post-coronary artery bypass grafts;

Metabolic disorders such as diabetes mellitus, nephrogenic diabetes insipidus, post-transplant diabetes mellitus, non-alcoholic fatty liver disease such as non-alcoholic steatohepatitis Miscellaneous conditions such as hypertension, or symptoms such as constipation, prevention of premature labour, neuroprotection in conditions such as cerebral ischemia The invention also relates to the use of a compound of the invention in the manufacture of a pharmaceutical composition agonising EP2 receptors, in particular a pharmaceutical composition for the treatment or prophylaxis of diseases alleviated by agonism of EP2 receptors, preferably a pharmaceutical composition for the treatment or prophylaxis of the diseases exemplified above.

In particular, the invention relates to the use of a compound of the invention in the manufacture of a pharmaceutical composition for the treatment or prophylaxis of an acute or chronic airway disease, such as but not limited to, bronchial asthma, chronic asthmatic disorders with reduced lung function and airway hyperreactivity, bronchial acute exacerbations, chronic bronchitis, acute respiratory distress syndrome, chronic obstructive pulmonary disorder (COPD), pulmonary artery hypertension (PAH) and pulmonary fibrosis or cystic fibrosis;

In a particularly preferred embodiment of the invention, in the above-mentioned uses the compound of the invention is a compound of the examples according to the invention.

Preferably, the invention relates to a method of treating or preventing one or more of the following diseases: bronchial asthma, chronic asthmatic disorders with reduced lung function and airway hyperreactivity, bronchial acute exacerbations, chronic bronchitis, acute respiratory distress syndrome, chronic obstructive pulmonary disorder (COPD) and idiopathic pulmonary fibrosis, cystic fibrosis and pulmonary artery hypertension comprising administering to a patient in need thereof a therapeutically effective amount of at least one of the compounds of the invention.

In the above methods, the patient is preferably a mammal, more preferably a human. Furthermore, in the above methods, at least one of the compounds of the invention can be used. Preferably, one or two of the compounds of the invention are used; more preferably, one of the compounds of the invention is used.

In a particularly preferred embodiment of the invention, the above methods of treating or preventing one of the above mentioned diseases comprise administering to a patient in need thereof a therapeutically effective amount of one compound of the examples according to the present invention.

Preferably, the pharmaceutical composition comprises one or two of the compounds of the invention. More preferable, the pharmaceutical composition comprises one of the compounds of the invention. The invention furthermore relates to a pharmaceutical composition, which comprises at least one of the compounds of the invention together with at least one pharmaceutically acceptable auxiliary.

Depending on the particular disease to be treated or prevented, additionally therapeutic agents, which are normally administered to treat or prevent that disease, may optionally be co-administered with the compounds of the invention.

In a preferred embodiment, at least one of the compounds of the invention is co-administered with at least one therapeutic agent selected from the group consisting of corticosteroids, anticholinergics, β2-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics.

In this respect, the "therapeutic agent" includes the corticosteroids, anticholinergics, β2-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics in form of the free compounds, the pharmaceutically acceptable salts thereof, the pharmaceutically acceptable derivatives thereof (e.g., but not limited to, ester derivatives, N-oxides etc.), the solvates (hydrates) thereof and the stereoisomers of the compounds, salts, derivatives and solvates.

Co-administration of at least one of the compounds of the invention with at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics can take place in form of a fixed combination, a non-fixed combination or a kit of parts.

A "fixed combination" is defined as a combination wherein the compound of the invention and the therapeutic agent intended for co-administration are present in one dosing unit or in a single entity. One example of a fixed combination is a pharmaceutical composition wherein the compound of the invention and the therapeutic agent are present in admixture for simultaneous administration. Another example of a fixed combination is a pharmaceutical composition wherein the compound of the invention and the therapeutic compound are present in one dosing unit without being in direct admixture (for example, in form of pellets, which are filled in a capsule, whereby a part of the pellets contains the compound of the invention and another part of the pellets contains the therapeutic agent).

A "non-fixed combination" or "kit of parts" is defined as a combination wherein the compound of the invention and the therapeutic agent are present in more than one dosing unit. In a non-fixed combination or a kit of parts the compound of the invention and the therapeutic compound are provided as separate formulations. They might be packaged and presented together as separate components of a combination pack for simultaneous, sequential or separate use in combination therapy. Simultaneous or sequential administration of the compound of the invention and the therapeutic agent are preferred. In case of sequential or separate administration of the compound of the invention and the therapeutic agent, the compound of the invention can be administered before or after administration of the therapeutic agent.

Sequential administration encompasses a short time period between the administration of the compound of the invention and the therapeutic agent or vice versa (for example, the time that is needed to swallow one tablet after the other).

Separate administration encompasses longer time periods between the administration of the compound of the invention and the therapeutic agent. In a preferred embodiment of the invention, the compound of the invention is administered while the therapeutic agent (or vice versa) still has an therapeutic effect on the patient being treated.

In a particularly preferred embodiment of the invention the co-administration of at least one of the compounds of the invention with at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics leads to a therapeutic effect that is greater than the sum of the therapeutic effects that will be achieved in case the compound of the invention respectively the additional therapeutic agent are given alone.

The type of formulation of the compound of the invention and the therapeutic agent of a non-fixed combination or a kit of parts can be identical, similar, i.e. both, the compound of the invention and the therapeutic agent are formulated in separate tablets or capsules, or can be different, i.e. suited for different administration forms, such as e.g. the compound of the invention is formulated as tablet or capsule and the therapeutic agent is formulated as powder, solution or suspension.

Accordingly, the invention additionally relates to a fixed combination, a non-fixed combination or kit of parts comprising at least one of the compounds of the invention, at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics, and at least one pharmaceutically acceptable auxiliary.

In a preferred embodiment, the abovementioned fixed combination, non-fixed combination or kit of parts comprise a compound of the invention (in particular the compound of the invention is one of the examples of the invention or a pharmaceutically acceptable salt thereof), a corticosteroid and at least one pharmaceutically acceptable auxiliary. In a particularly preferred embodiment, the abovementioned fixed combination, non-fixed combination or kit of parts comprise:
a compound of the invention and budesonide,
a compound of the invention and fluticasone,
a compound of the invention and beclometasone,
a compound of the invention and mometasone,
a compound of the invention and triamcinolone acetonide, or
a compound of the invention and ciclesonide,
and at least one pharmaceutically acceptable auxiliary.

In a preferred embodiment, the pharmaceutically acceptable derivative of fluticasone is fluticasone-17-propionate. In another preferred embodiment, the pharmaceutically acceptable derivative of beclometasone is beclometasone 17, 21-dipropionate ester. In a preferred embodiment, the pharmaceutically acceptable derivative of mometasone is mometasone furoate.

The combination comprising a compound of the invention and a corticosteroid preferably is for the treatment and prophylaxis of bronchial asthma, COPD, allergic rhinitis, eosinophilic esophagitis or a dermatological disease, such as for example atopic dermatitis. Preferably the corticosteroid is used for intranasal, inhaled or (in case of a dermatological disease) transdermal administration; in severe cases, the corticosteroid may also be used orally.

In a preferred embodiment, the abovementioned fixed combination, non-fixed combination or kit of parts comprise a compound of the invention (in particular the compound of the invention is one of the examples of the invention or a pharmaceutically acceptable salt thereof), an anticholinergic and at least one pharmaceutically acceptable auxiliary. In a particularly preferred embodiment, the abovementioned fixed combination, non-fixed combination or kit of parts comprise:
a compound of the invention and glycopyrronium bromide,
a compound of the invention and aclidinium bromide,
a compound of the invention and tiotropium bromide, or
a compound of the invention and ipratropium bromide,
and at least one pharmaceutically acceptable auxiliary.

In a preferred embodiment, the stereoisomer of glycopyrronium bromide is (R,R)-glycopyrronium bromide. In a preferred embodiment, tiotropium bromide is used in form of its monohydrate.

Preferably, the anticholinergic is for inhaled administration. The combination comprising a compound of the invention and an anticholinergic is preferably for the treatment or prophylaxis of COPD.

In a preferred embodiment, the abovementioned fixed combination, non-fixed combination or kit of parts comprise a compound of the invention (in particular the compound of the invention is one of the examples of the invention or a pharmaceutically acceptable salt thereof), a $\beta_2$-adrenoreceptor agonist and at least one pharmaceutically acceptable auxiliary. In a particularly preferred embodiment, the abovementioned fixed combination, non-fixed combination or kit of parts comprise:
a compound of the invention and salbutamol,
a compound of the invention and milveterol,
a compound of the invention and indacaterol,
a compound of the invention and carmoterol,
a compound of the invention and salmeterol,
a compound of the invention and formoterol,
and at least one pharmaceutically acceptable auxiliary.

In a preferred embodiment, the pharmaceutically acceptable salt of salbutamol is salbutamol sulfate. In a preferred embodiment, the pharmaceutically acceptable salt of milveterol is milveterol hydrochloride.

In a preferred embodiment, the pharmaceutically acceptable salt of carmoterol is carmoterol hydrochloride. In a preferred embodiment, the pharmaceutically acceptable salt of salmeterol is salmeterol xinafoate. In another preferred embodiment, the pharmaceutically acceptable salt of formoterol is formoterol hemifumarate monohydrate. In another preferred embodiment, the stereoisomer of formoterol is R,R-formoterol. In another preferred embodiment, the pharmaceutically acceptable salt of R,R-formoterol is R,R-formoterol L-tartrate.

Preferably the β2-adrenoreceptor agonist is a long-acting β2-adrenoreceptor agonist; particularly preferred in this respect are those β2-adrenoreceptor agonists having a therapeutic effect over a 12-24 hours period.

Preferably, the combination comprising a compound of the invention and a β2-adrenoreceptor agonist is for the treatment or prophylaxis of bronchial asthma and COPD.

In a preferred embodiment, the abovementioned fixed combination, non-fixed combination or kit of parts comprise a compound of the invention (in particular the compound of the invention is one of the examples of the invention), a H1 receptor antagonist and at least one pharmaceutically acceptable auxiliary. In a particularly preferred embodiment, the abovementioned fixed combination, non-fixed combination or kit of parts comprise:
a compound of the invention and azelastine,
a compound of the invention and olopatadine,
a compound of the invention and loratadine,
a compound of the invention and desloratadine, or
a compound of the invention and cetirizine,
and at least one pharmaceutically acceptable auxiliary.

In a preferred embodiment, the pharmaceutically acceptable salt of azelastine is is azelastine hydrochloride. In a preferred embodiment, the pharmaceutically acceptable salt of olapatadine is olapatadine hydrochloride. In a preferred embodiment, the pharmaceutically acceptable salt of cetirizine is cetirizine dihydrochloride. In a preferred embodiment, the stereoisomer of cetirizine is levocetirizine. In another preferred embodiment, the pharmaceutically acceptable salt of levocetirizine is levocetirizine dihydrochloride.

The combination comprising a compound of the invention and a H1 receptor agonist is preferably for the treatment or prophylaxis of allergic rhinitis.

In a preferred embodiment, the abovementioned fixed combination, non-fixed combination or kit of parts comprise a compound of the invention (in particular the compound of the invention is one of the examples of the invention), a leukotriene receptor antagonist and at least one pharmaceutically acceptable auxiliary. In a particularly preferred embodiment, the abovementioned fixed combination, non-fixed combination or kit of parts comprise:
a compound of the invention and montelukast,
a compound of the invention and pranlukast, or
a compound of the invention and zafirlukast,
and at least one pharmaceutically acceptable auxiliary.

In a preferred embodiment, the pharmaceutically acceptable salt of montelukast is montelukast sodium. In another preferred embodiment, pranlukast is used in form of its monohydrate.

The combination comprising a compound of the invention and a leukotriene receptor antagonist is preferably for the treatment or prophylaxis of bronchial asthma or allergic rhinitis.

In a preferred embodiment, the abovementioned fixed combination, non-fixed combination or kit of parts comprise a compound of the invention (in particular the compound of the invention is one of the examples of the invention or a pharmaceutically acceptable salt thereof), a 5-lipoxygenase inhibitor and at least one pharmaceutically acceptable auxiliary. In a particularly preferred embodiment, the abovementioned fixed combination, non-fixed combination or kit of parts comprise:
a compound of the invention and zileuton, and at least one pharmaceutically acceptable auxiliary.

The combination comprising a compound of the invention and a 5-lipoxygenase inhibitor is preferably for the treatment or prophylaxis of bronchial asthma.

In a preferred embodiment, the abovementioned fixed combination, non-fixed combination or kit of parts comprise a compound of the invention (in particular the compound of the invention is one of the examples of the invention or a pharmaceutically acceptable salt thereof), an endothelin antagonist and at least one pharmaceutically acceptable auxiliary. In a particularly preferred embodiment, the abovementioned fixed combination, non-fixed combination or kit of parts comprise:
a compound of the invention and bosentan,
a compound of the invention and ambrisentan,
a compound of the invention and atrasentan,
a compound of the invention and darusentan,
a compound of the invention and clazosentan, or
a compound of the invention and avosentan,
and at least one pharmaceutically acceptable auxiliary.

In another preferred embodiment, bosentan is used in form of its monohydrate. In another preferred embodiment the pharmaceutically acceptable salt of clazosentan is the disodium salt of clazosentan. In another preferred embodiment the pharmaceutically acceptable salts of atrasentan are atrasentan hydrochloride or the sodium salt of atrasentan. In another preferred embodiment the R-enantiomer of atrasentan is used. In another preferred embodiment the S-enantiomer of darusentan is used.

The combination comprising a compound of the invention and an endothelin antagonist is preferably for the treatment or prophylaxis of bronchial asthma.

In a preferred embodiment, the abovementioned fixed combination, non-fixed combination or kit of parts comprise a compound of the invention (in particular the compound of the invention is one of the examples of the invention or a pharmaceutically acceptable salt thereof), a type 4 phosphodiesterase inhibitor and at least one pharmaceutically acceptable auxiliary. In a particularly preferred embodiment, the abovementioned fixed combination, non-fixed combination or kit of parts comprise:
a compound of the invention and roflumilast,
a compound of the invention and roflumilast-N-oxide,
a compound of the invention and oglemilast,
a compound of the invention and tipelukast,
and at least one pharmaceutically acceptable auxiliary.

The combination comprising a compound of the invention and a type 4 phosphodiesterase inhibitor is preferably for the treatment or prophylaxis of bronchial asthma and COPD.

In a particularly preferred embodiment, the above-mentioned fixed combination, non-fixed combination or kit of parts comprise: a compound of the invention (in particular the compound of the invention is one of the examples of the invention or a pharmaceutically acceptable salt thereof), a type 4 phosphodiesterase inhibitor and at least one pharmaceutically acceptable auxiliary. In a particularly preferred embodiment, the abovementioned fixed combination, non-fixed combination or kit of parts comprise
a compound of the invention and sildenafil,
a compound of the invention and vardenafil,
a compound of the invention and tadalafil,
a compound of the invention and udenafil,
a compound of the invention and avanafil,
and at least one pharmaceutically acceptable auxiliary.

In another preferred embodiment, the pharmaceutically acceptable salts of sildenafil are sildenafil hemi-citrate, sildenafil citrate and sildenafil mesilate; particularly preferred is the citrate salt of sildenafil. In another preferred embodiment, the pharmaceutically acceptable salts of vardenafil are vardenafil hydrochloride or vardenafil dihydrochloride. In another preferred embodiment, the pharmaceutically acceptable salt of avanafil is avanafil besilate.

In a preferred embodiment, the abovementioned fixed combination, non-fixed combination or kit of parts comprise a compound of the invention (in particular the compound of the invention is one of the examples of the invention or a pharmaceutically acceptable salt thereof), theophylline and at least one pharmaceutically acceptable auxiliary. In a particularly preferred embodiment, the abovementioned fixed combination, non-fixed combination or kit of parts comprise: a compound of the invention and theophylline, and at least one pharmaceutically acceptable auxiliary.

The combination comprising a compound of the invention and theophylline is preferably for the treatment or prophylaxis of bronchial asthma and COPD.

In a preferred embodiment, the abovementioned fixed combination, non-fixed combination or kit of parts comprise a compound of the invention (in particular the compound of the invention is one of the examples of the invention or a pharmaceutically acceptable salt thereof), an immune modulator and at least one pharmaceutically acceptable auxiliary. In a particularly preferred embodiment, the abovementioned fixed combination, non-fixed combination or kit of parts comprise:
a compound of the invention and omalizumab, or
a compound of the invention and lumiliximab,
and at least one pharmaceutically acceptable auxiliary.

The combination comprising a compound of the invention and one of the abovementioned immune modulators is preferably for the treatment or prophylaxis of bronchial asthma or eosinophilic esophagitis.

In a preferred embodiment, the abovementioned fixed combination, non-fixed combination or kit of parts comprise a compound of the invention (in particular the compound of the invention is one of the examples of the invention or a pharmaceutically acceptable salt thereof), a cytokine inhibitor and at least one pharmaceutically acceptable auxiliary. In a particularly preferred embodiment, the abovementioned fixed combination, non-fixed combination or kit of parts comprise:
a compound of the invention and suplatast,
a compound of the invention and mepolizumab,
a compound of the invention and etanercept, or
a compound of the invention and maraviroc,
and at least one pharmaceutically acceptable auxiliary.

In a preferred embodiment suplatast is used in form of its tosilate salt.

The combination comprising a compound of the invention and one of the abovementioned cytokine inhibitors may be preferably used for the treatment or prophylaxis of bronchial asthma, allergic rhinitis or eosinophilic esophagitis.

In a preferred embodiment, the abovementioned fixed combination, non-fixed combination or kit of parts comprise a compound of the invention (in particular the compound of the invention is one of the examples of the invention or a pharmaceutically acceptable salt thereof), a HMG-CoA reductase inhibitor and at least one pharmaceutically acceptable auxiliary. In a particularly preferred embodiment, the abovementioned fixed combination, non-fixed combination or kit of parts comprise:
a compound of the invention and lovastatin,
a compound of the invention and pravastatin,
a compound of the invention and simvastatin,
a compound of the invention and atorvastatin,
a compound of the invention and fluvastatin,
a compound of the invention and rosuvastatin,
a compound of the invention and pitavastatin,
a compound of the invention and bervastatin,
a compound of the invention and dalvastatin, or
a compound of the invention and glenvastatin,
and at least one pharmaceutically acceptable auxiliary.

In a preferred embodiment the pharmaceutically acceptable salts of pravastatin are the potassium, lithium, sodium and hemi-calcium salt of pravastatin. A particularly preferred pharmaceutically acceptable salt of pravastatin is the sodium salt of pravastatin. In a preferred embodiment the pharmaceutically acceptable salt of simvastatin is the sodium salt of simvastatin. In a preferred embodiment the pharmaceutically acceptable salts of atorvastatin are the potassium, sodium and the hemi-calcium salt of atorvastatin. A particularly preferred pharmaceutically acceptable salt of atorvastatin is the hemi-calcium salt of atorvastatin. As an example for a hydrate of atorvastatin may be mentioned the trihydrate and the sesquihydrate of the hemi-calcium salt of atorvastatin. In a preferred embodiment of the pharmaceutically acceptable salt of fluvastatin is the sodium salt of fluvastatin. In a preferred embodiment the pharmaceutically acceptable salts of rosuvastatin are the potassium, lithium, sodium, hemi-magnesium and the hemi-calcium salt of rosuvastatin. A particularly preferred pharmaceutically acceptable salt of rosuvastatin is the hemi-calcium salt of rosuvastatin. Another particularly preferred pharmaceutically acceptable salt of rosuvastatin is the sodium salt of rosuvastatin. In a preferred embodiment the pharmaceutically acceptable salts of pitavastatin are the potassium, sodium and the hemi-calcium salt of pitavastatin. A particularly preferred pharmaceutically acceptable salt of pitavastatin is the hemi-calcium salt of pitavastatin.

The combination comprising a compound of the invention and a HMG-CoA reductase inhibitor is preferably for the treatment or prophylaxis of COPD.

In a preferred embodiment, the abovementioned fixed combination, non-fixed combination or kit of parts comprise a compound of the invention (in particular the compound of the invention is one of the examples of the invention), a lung surfactant and at least one pharmaceutically acceptable auxiliary. In a particularly preferred embodiment, the abovementioned fixed combination, non-fixed combination or kit of parts comprise:
a compound of the invention and lusupultide,
a compound of the invention and poracant alfa,
a compound of the invention and sinapultide,
a compound of the invention and beracant,
a compound of the invention and bovacant,
a compound of the invention and colfosceril palmitate,
a compound of the invention and surfactant-TA, or
a compound of the invention and calfacant,
and at least one pharmaceutically acceptable auxiliary.

The combination comprising a compound of the invention and a lung surfactant is preferably for the treatment or prophylaxis of bronchial asthma or COPD.

In a preferred embodiment, the abovementioned fixed combination, non-fixed combination or kit of parts comprise a compound of the invention (in particular the compound of the invention is one of the examples of the invention or a pharmaceutically acceptable salt thereof), an antibiotic and at least one pharmaceutically acceptable auxiliary. In a particularly preferred embodiment, the abovementioned fixed combination, non-fixed combination or kit of parts comprise:
a compound of the invention and amoxicillin,
a compound of the invention and ampicillin,
a compound of the invention and levofloxacin,
a compound of the invention and clarithromycin,
a compound of the invention and ciprofloxacin,
a compound of the invention and telithromycin, or
a compound of the invention and azithromycin,
and at least one pharmaceutically acceptable auxiliary.

In a preferred embodiment, amoxicillin is used in form of its trihydrate. In another preferred embodiment, ampicillin is used in form of its trihydrate. In another preferred embodiment, the pharmaceutically acceptable salt of ampicillin is ampicillin natrium. In another preferred embodiment levofloxacin is used in form of its hemi hydrate. In another preferred embodiment, the pharmaceutically acceptable salt of ciprofloxacin is ciprofloxacin hydrochloride monohydrate. In another preferred embodiment, azithromycin is used in form of its monohydrate.

The combination comprising a compound of the invention and an antibiotic is preferably for the treatment or prophylaxis of exacerbations associated with bronchial asthma and COPD.

In a preferred embodiment, the abovementioned fixed combination, non-fixed combination or kit of parts comprise a compound of the invention (in particular the compound of the invention is one of the examples of the invention or a pharmaceutically acceptable salt thereof), a corticosteroid, a $\beta_2$-adrenoceptor agonist and at least one pharmaceutically acceptable auxiliary. In a particularly preferred embodiment, the abovementioned fixed combination, non-fixed combination or kit of parts comprise:
a compound of the invention, budesonide and salbutamol,
a compound of the invention, budesonide and milveterol,
a compound of the invention, budesonide and indacaterol,
a compound of the invention, budesonide and carmoterol,
a compound of the invention, budesonide and salmeterol,
a compound of the invention, budesonide and formoterol,
a compound of the invention, fluticasone and salbutamol,
a compound of the invention, fluticasone and milveterol,
a compound of the invention, fluticasone and indacaterol,
a compound of the invention, fluticasone and carmoterol,
a compound of the invention, fluticasone and salmeterol,
a compound of the invention, fluticasone and formoterol,
a compound of the invention, beclometasone and salbutamol,
a compound of the invention, beclometasone and milveterol,
a compound of the invention, beclometasone and indacaterol,
a compound of the invention, beclometasone and carmoterol,
a compound of the invention, beclometasone and salmeterol,
a compound of the invention, beclometasone and formoterol,
a compound of the invention, mometasone and salbutamol,
a compound of the invention, mometasone and milveterol,
a compound of the invention, mometasone and indacaterol,
a compound of the invention, mometasone and carmoterol,
a compound of the invention, mometasone and salmeterol,
a compound of the invention, mometasone and formoterol,
a compound of the invention, triamcinolone acetonide and salbutamol,
a compound of the invention, triamcinolone acetonide and milveterol, a compound of the invention, triamcinolone acetonide and indacaterol,
a compound of the invention, triamcinolone acetonide and carmoterol,
a compound of the invention, triamcinolone acetonide and salmeterol,
a compound of the invention, triamcinolone acetonide and formoterol,
a compound of the invention, ciclesonide and salbutamol,
a compound of the invention, ciclesonide and milveterol,
a compound of the invention, ciclesonide and indacaterol,
a compound of the invention, ciclesonide and carmoterol,
a compound of the invention, ciclesonide and salmeterol, or
a compound of the invention, ciclesonide and formoterol,
and at least one pharmaceutically acceptable auxiliary.

In a preferred embodiment, the pharmaceutically acceptable salt of salbutamol is salbutamol sulfate. In a preferred embodiment, the pharmaceutically acceptable salt of milveterol is milveterol hydrochloride. In a preferred embodiment, the pharmaceutically acceptable salt of carmoterol is carmoterol hydrochloride. In a preferred embodiment, the pharmaceutically acceptable salt of salmeterol is salmeterol xinafoate. In another preferred embodiment, the pharmaceutically acceptable salt of formoterol is formoterol hemifumarate monohydrate. In another preferred embodiment, the stereoisomer of formoterol is R,R-formoterol. In another preferred embodiment, the pharmaceutically acceptable salt of R,R-formoterol is R,R-formoterol L-tartrate. In a preferred embodiment, the pharmaceutically acceptable salt of fluticasone is fluticasone-17-propionate. In another preferred embodiment, the pharmaceutically acceptable salt of beclometasone is beclometasone dipropionate. In a preferred embodiment, the pharmaceutically acceptable salt of mometasone is mometasone furoate.

In a preferred embodiment, the abovementioned fixed combination, non-fixed combination or kit of parts comprise a compound of the invention (in particular the compound of the invention is one of the examples of the invention or a pharmaceutically acceptable salt thereof), a $\beta_2$-adrenoceptor agonist, an anticholinergic and at least one pharmaceutically acceptable auxiliary. In a particularly preferred embodiment, the abovementioned fixed combination, non-fixed combination or kit of parts comprise:
a compound of the invention, salbutamol and glycopyrronium bromide,
a compound of the invention, salbutamol and aclidinium bromide,
a compound of the invention, salbutamol and tiotropium bromide,
a compound of the invention, salbutamol and ipratropium bromide,
a compound of the invention, milveterol and glycopyrronium bromide,
a compound of the invention, milveterol and aclidinium bromide,
a compound of the invention, milveterol and tiotropium bromide,
a compound of the invention, milveterol and ipratropium bromide,
a compound of the invention, salmeterol and glycopyrronium bromide,
a compound of the invention, salmeterol and aclidinium bromide,
a compound of the invention, salmeterol and tiotropium bromide,
a compound of the invention, salmeterol and ipratropium bromide,
a compound of the invention, formoterol and glycopyrronium bromide,
a compound of the invention, formoterol and aclidinium bromide,
a compound of the invention, formoterol and tiotropium bromide,
a compound of the invention, formoterol and ipratropium bromide,
a compound of the invention, indacaterol and glycopyrronium bromide,
a compound of the invention, indacaterol and aclidinium bromide,
a compound of the invention, indacaterol and tiotropium bromide,
a compound of the invention, indacaterol and ipratropium bromide,
a compound of the invention, carmoterol and glycopyrronium bromide,
a compound of the invention, carmoterol and aclidinium bromide,
a compound of the invention, carmoterol and tiotropium bromide, or
a compound of the invention, carmoterol and ipratropium bromide,
and at least one pharmaceutically acceptable auxiliary.

In a preferred embodiment, the pharmaceutically acceptable salt of salbutamol is salbutamol sulfate. In a preferred embodiment, the pharmaceutically acceptable salt of milveterol is milveterol hydrochloride.

In a preferred embodiment, the pharmaceutically acceptable salt of carmoterol is carmoterol hydrochloride. In a preferred embodiment, the pharmaceutically acceptable salt of salmeterol is salmeterol xinafoate. In another preferred embodiment, the pharmaceutically acceptable salt of formoterol is formoterol hemifumarate monohydrate. In another preferred embodiment, the stereoisomer of formoterol is R,R-formoterol. In another preferred embodiment, the pharmaceutically acceptable salt of R,R-formoterol is R,R-formoterol L-tartrate. In a preferred embodiment, the stereoisomer of glycopyrronium bromide is (R,R)-glycopyrronium bromide. In a preferred embodiment, tiotropium bromide is used in form of its monohydrate.

In a preferred embodiment, the abovementioned fixed combination, non-fixed combination or kit of parts comprise a compound of the invention (in particular the compound of the invention is one of the examples of the invention or a pharmaceutically acceptable salt thereof), a corticosteroid, an anticholinergic and at least one pharmaceutically acceptable auxiliary. In a particularly preferred embodiment, the abovementioned fixed combination, non-fixed combination or kit of parts comprise:
a compound of the invention, budesonide and glycopyrronium bromide,
a compound of the invention, budesonide and aclidinium bromide,
a compound of the invention, budesonide and tiotropium bromide,
a compound of the invention, budesonide and ipratropium bromide,
a compound of the invention, fluticasone and glycopyrronium bromide,
a compound of the invention, fluticasone and aclidinium bromide,
a compound of the invention, fluticasone and tiotropium bromide,
a compound of the invention, fluticasone and ipratropium bromide, a compound of the invention, beclometasone and glycopyrronium bromide,
a compound of the invention, beclometasone and aclidinium bromide,
a compound of the invention, beclometasone and tiotropium bromide,
a compound of the invention, beclometasone and ipratropium bromide,
a compound of the invention, mometasone and glycopyrronium bromide,
a compound of the invention, mometasone and aclidinium bromide,
a compound of the invention, mometasone and tiotropium bromide,
a compound of the invention, mometasone and ipratropium bromide,
a compound of the invention, triamcinolone acetonide and glycopyrronium bromide,
a compound of the invention, triamcinolone acetonide and aclidinium bromide,
a compound of the invention, triamcinolone acetonide and tiotropium bromide,
a compound of the invention, triamcinolone acetonide and ipratropium bromide,
a compound of the invention, ciclesonide and glycopyrronium bromide,
a compound of the invention, ciclesonide and aclidinium bromide,
a compound of the invention, ciclesonide and tiotropium bromide, or
a compound of the invention, ciclesonide and ipratropium bromide,
and at least one pharmaceutically acceptable auxiliary.

In a preferred embodiment, the pharmaceutically acceptable salt of fluticasone is fluticasone-17-propionate. In another preferred embodiment, the pharmaceutically acceptable salt of beclometasone is beclometasone dipropionate. In a preferred embodiment, the pharmaceutically acceptable salt of mometasone is mometasone furoate. In a preferred embodiment, the stereoisomer of glycopyrronium bromide is (R,R)-glycopyrronium bromide. In a preferred embodiment, tiotropium bromide is used in form of its monohydrate.

The abovementioned triple combinations may preferably be used in the treatment or prophylaxis of bronchial asthma or COPD.

Exemplary combinations, in particular for transdermal administration (for example versus atopic dermatitis or psoriasis), may include a compound of the invention and an immunosuppressant, for example a calcineurin inhibitor, such as pimecrolimus or tacrolimus.

Therefore, in another preferred embodiment, the abovementioned fixed combination, non-fixed combination or kit of parts comprise a compound of the invention (in particular the compound of the invention is one of the examples of the invention or a pharmaceutically acceptable salt thereof), an immunosuppressant and at least one pharmaceutically acceptable auxiliary. In a particularly preferred embodiment, the above mentioned fixed combination, non-fixed combination or kit of parts comprises:
a compound of the invention and pimecrolimus,
a compound of the invention and tacrolimus,
a compound of the invention and methotrexate,
a compound of the invention and ascomycin, or
a compound of the invention and cyclosporin A,
and at least one pharmaceutically acceptable auxiliary.

The externally topically (transdermal) administrable immunosuppressant can be administered or administrable in an external-topical composition separately from the compound of the invention (non-fixed combination or kit of parts) or it can be contained with the compound of the invention in a combined externally-topically administrable composition (fixed combination). In a preferred embodiment the externally topically administrable composition is a cream containing pimecrolimus at ca. 1% w/w concentration. In another preferred embodiment the externally topically administrable composition is an ointment containing tacrolimus at from about 0.03% to about 0.1% w/w concentration).

Other combinations for external topical administration, in particular for the treatment or prophylaxis of atopic dermatitis and psoriasis, may include a compound of the invention and a corticosteroid. Beside the corticosteroid combinations mentioned above also the following corticosteroid combinations may be useful.

In another preferred embodiment, the abovementioned fixed combination, non-fixed combination or kit of parts comprise a compound of the invention (in particular the compound of the invention is one of the examples of the invention or a pharmaceutically acceptable salt thereof), a corticosteroid and at least one pharmaceutically acceptable auxiliary.

In a particularly preferred embodiment, the above mentioned fixed combination, non-fixed combination or kit of parts comprises:
a compound of the invention and prednisolone,
a compound of the invention and dexamethasone,
a compound of the invention and clobetasol,
a compound of the invention and betamethasone, or
a compound of the invention and hydrocortisone,
and at least one pharmaceutically acceptable auxiliary.

In another preferred embodiment, the abovementioned corticosteroids are used in form of an ester, such as, for example, prednisolone valerate acetate, hydrocortisone butyrate, hydrocortisone acetate, dexamethasone valerate, dexamethasone propionate, dexamethasone dipropionate, betamethasone butyrate propionate or prednisolone valerate acetate. In another preferred embodiment the pharmaceutically acceptable derivative of clobetasol is clobetasol propionate.

Further combinations for external topical (transdermal) administration, in particular for the treatment of psoriasis, may include a compound of the invention and a vitamin D analogue.

Therefore, in another preferred embodiment the abovementioned fixed combination, non-fixed combination or kit of parts comprise a compound of the invention (in particular the compound of the invention is one of the examples of the invention or a pharmaceutically acceptable salt thereof), a vitamin D analogue and at least one pharmaceutically acceptable auxiliary.

In a particularly preferred embodiment, the above mentioned fixed combination, non-fixed combination or kit of parts comprises:
a compound of the invention and calcitriol,
a compound of the invention and calcipotriol, or
a compound of the invention and tacalcitol,
and at least one pharmaceutically acceptable auxiliary.

The pharmaceutical compositions according to the invention—if not indicated otherwise explicitly—preferably contain the compound or compounds of the invention in a total amount of from 0.1 to 99.9 wt %, more preferably 5 to 95 wt %, in particular 20 to 80 wt %. In case at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics is present in the pharmaceutical compositions of the invention, the total amount of said therapeutic agent or therapeutic agents in the pharmaceutical compositions is—if not indicated otherwise explicitly—preferably in the range of from 0.1 to 99.9 wt %, more preferably 5 to 95 wt %, in particular 20 to 80 wt %, under the provision that the total amount of the compound or compounds of the invention and the therapeutic agent or therapeutic agents is less than 100 wt %.

As pharmaceutically acceptable auxiliaries, any auxiliaries known to be suitable for preparing pharmaceutical compositions/formulations can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The pharmaceutical compositions/formulations can be formulated, for example, into tablets, coated tablets (dragees), pills, cachets, capsules (caplets), granules, powders, suppositories, solutions (e.g., but not limited to, sterile solutions), emulsions, suspensions, ointments, creams, lotions, pastes, oils, gels, sprays and patches (e.g., but not limited to, transdermal therapeutic systems). Additionally, the pharmaceutical compositions can be prepared as e.g. liposome delivery systems, systems in which the compound of the invention is coupled to monoclonal antibodies and systems in which the compound of the invention is coupled to polymers (e.g., but not limited to, soluble or biodegradable polymers).

The pharmaceutical compositions/formulations can be manufactured in a manner known to a person skilled in the art, e.g. by dissolving, mixing, granulating, dragee-making, levigating, emulsifying, encapsulating, entrapping or lyophilizing processes.

The selected formulation depends inter alia on the route of administering the pharmaceutical composition. The pharmaceutical compositions/formulations of the invention can be administered by any suitable route, for example, by the oral, sublingual, buccal, intravenous, intraarterial, intramuscular, subcutaneous, intracutaneous, topical, transdermal, intranasal, intraocular, intraperitoneal, intrasternal, intracoronary, transurethral, rectal or vaginal route, by inhalation or by insufflation. Oral administration of the compounds of the invention is preferred.

In case of non-fixed combinations or kit of parts comprising at least one of the compounds of the invention and at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics, the compound of the invention and the therapeutic agent may be administered by the same route, e.g., without limitation, orally, or by different routes, e.g., without limitation, the compound of the invention can be administered orally and the therapeutic agent can be administered for example, subcutaneous or by inhalation.

In case of pharmaceutical compositions comprising at least one of the compounds of the invention and at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics, the compound of the invention and the therapeutic agent may be formulated together into the same dosage form (e.g., but not limited to, tablets), separately into the same dosage form (e.g., but not limited to, tablets), or into different dosage forms (without limitation e.g. the compound of the invention may be formulated as tablet and the therapeutic agent may be formulated as powder, solution or suspension).

Tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the compound of the invention to a biodegradable polymer.

Administration by inhalation or instillation is preferably made by using an aerosol. The aerosol is a liquid-gaseous dispersion, a solid-gaseous dispersion or a mixed liquid/solid-gaseous dispersion. The aerosol may be generated by means of aerosol-producing devices such as dry powder inhalers (DPIs), pressurized metered dose inhalers (PMDIs) and nebulizers. Depending on the kind of the compound of the invention to be administered, the aerosol-producing device can contain the compound in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (cosolvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 µm, more preferably it is in the range of from 0.5 to 10 µm, in particular in the range of from 2 to 6 µm (D50 value, measured by laser diffraction).

Specific aerosol-producing devices which may be used for inhaled administration include, but are not limited to, Cyclohaler®, Diskhaler®, Rotadisk®, Turbohaler®, Autohaler®, Novolizer®, Easyhaler®, Aerolizer®, Jethaler®, Diskus®, Ultrahaler® and Mystic® inhalers. The aerosol-producing devices may be combined with spacers or expanders, e.g. Aerochamber®, Nebulator®, Volumatic® and Rondo®, for improving inhalation efficiency.

In case of topical administration, suitable pharmaceutical formulations are, for example, ointments, creams, lotions, pastes, gels, powders, solutions, emulsions, suspensions, oils, sprays and patches (e.g., but not limited to, transdermal therapeutic systems).

For parenteral modes of administration such as, for example, intravenous, intraarterial, intramuscular, subcutaneous, intracutaneous, intraperitoneal and intrasternal administration, preferably solutions (e.g., but not limited to, sterile solutions, isotonic solutions) are used. They are preferably administered by injection or infusion techniques.

In case of intranasal administration, for example, sprays and solutions to be applied in drop form are preferred formulations.

For intraocular administration, solutions to be applied in drop form, gels and ointments are exemplified formulations.

In case of co-administration of at least one compound of the invention with at least one therapeutic agent selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics, in form of a fixed combination, non-fixed combination or kit of parts the dose of the compound of the invention as well as the dose of the therapeutic agent will be in a range customary for the mono-therapy, it more likely being possible, on account of the individual action, which are mutually positively influencing and reinforcing, to reduce the respective doses in case of co-administration of the compound(s) of the invention and the therapeutic agent.

Generally, the pharmaceutical compositions according to the invention can be administered such that the dose of the compound of the invention is in the range customary for EP2 Agonists. In particular, a dose in the range of from 0.05 to 500 mg, preferably 0.1 to 200 mg of the compound of the invention per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical composition can be administered in a single dose per day or in multiple subdoses, for example, 2 to 4 doses per day. A single dose unit of the pharmaceutical composition can contain e.g. from 0.05 mg to 500 mg, preferably 0.1 mg to 200 mg, more preferably 0.1 mg to 100 mg, most preferably 0.1 mg to 10 mg, of the compound of the invention.

In case of co-administration of at least one compound of the invention and at least one therapeutic compound selected from the group consisting of corticosteroids, anticholinergics, $\beta_2$-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, immunosuppressants, immune modulators, cytokine inhibitors, vitamin D analogues, HMG-CoA reductase-inhibitors, lung surfactants and antibiotics, in form of a fixed combination, a non-fixed combination or a kit of parts a single dose unit of the respective pharmaceutical composition/formulation can contain e.g. from 0.05 mg to 500 mg, preferably 0.1 mg to 200 mg, more preferably 0.1 to 100 mg of the compound of the invention and/or e.g. from 0.01 mg to 4000 mg, preferably 0.1 mg to 2000 mg, more preferably 0.5 mg to 1000 mg, most preferably 1 mg to 500 mg, of the therapeutic agent, depending on the therapeutic agent being used, the disease to be treated and the administration route selected. Preferably, the at least one compound of the invention and the at least one therapeutic agent are present in the pharmaceutical compositions/formulations in a weight ratio of from 1000:1 to 1:1000, more preferably in a weight ratio of from 100:1 to 1:100, even more preferably in a weight ratio of from 25:1 to 1:25.

Furthermore, the pharmaceutical composition may be adapted to weekly, monthly or even more infrequent administration, for example by using an implant, e.g. a subcutaneous or intramuscular implant, by using the compound of the invention in form of a sparingly soluble salt or by using the compound of the invention coupled to a polymer.

Biological Investigations

Method for Measuring Inhibition of PGE2 Binding to the Human Prostanoid Receptor EP2:

Human EP2 receptor equilibrium competition binding assays were performed according to Abramovitz et al. (M. Abramovitz et al. 2000, Biochimica et Biophysica Acta 1483: 285-293) in a final incubation volume of 100 microL in 50 milliM Bis-Tris, pH6.0 in 96-well plates. Radiolabelled Prostaglandin E2 ($PGE_2$) (1 nanoM [$^3$H]-$PGE_2$ purchased from Perkin Elmer) was added to the assay as competitive ligand. Test compounds stored as Dimethylsulfoxide (DMSO) stock solutions were added to the assay in serial dilutions in assay buffer while keeping the final DMSO concentration equal in each sample. The reaction was initiated by addition of membrane proteins harbouring human EP2 receptor (ChemiSCREEN™ membrane preparation recombinant human EP2 prostanoid receptor that was purchased by Millipore). Total binding was determined in the absence of test compound or $PGE_2$ and non-specific binding was determined in the presence of 1 microM $PGE_2$. Incubations were conducted for 60 minutes at room temperature until equilibrium was reached and terminated by filtration through GF/B filter (Perkin Elmer) prewetted with 0.3% PEI solution. Unbound radiolabelled $PGE_2$ was removed by 8 wash cycles with the same buffer under ice-cold conditions and the filters containing the residual radioactivity were dried for 60 minutes at 60° C. In order to measure the filter bound radioactivity, 40 microL microscint (scintillation liquid) was added to each filter and the chemiluminescence was determined by TopCount-NTX™. The specific binding was calculated by subtracting non-specific binding from each sample. Percent inhibition by test compounds was calculated based on specific binding without test compound. Each sample was measured in triplicates per experiment and for the calculation of the $pIC_{50}$ at least 2 independent experiments were performed. Determination of half maximal inhibiting concentration ($IC_{50}$) was performed with GraphPad Prism Software.

For the following compounds the EP2 binding values [determined as $-\log IC_{50}=pIC_{50}$] between 5.7 and 6.7, between 7 and 7.9 and between 8 and 8.9 have been determined. The numbers of the compounds correspond to the examples numbers.

EP2 Binding Assay (PGE2 Displacement): $pIC_{50}$ Values

| 5.7-6.9 | 7-7.9 | 8-8.9 |
|---|---|---|
| Example 23, 20, 21 | Example 6, 8, 7, 16, 22 | Example 5, 10, 3, 1, 19, 2, 9, 15, 13, 14, 4, 11, 17 |

Method for Measuring cAMP Release in Human EP2 Stably Transfectant Cells:

The potency and efficacy of EP2 agonists have been determined via measuring cAMP release in stably transfectant CHO-K1 cell expressing the human prostanoid receptor EP2 and luciferase enzyme regulated via a 6 times CRE (cAMP response element) containing transcriptional promoter. CHOp6CreLuc-huEP2 cells were seeded into 384-well plate (1000 cells per well) in DMEM/F12 (Dulbecco's Modified Eagle Medium/Nutrient Mixture F12) cell culture medium containing 2% FCS (Fetal Calf Serum) and 500 µg/ml G418 24 hours prior to the experiment. Test compound was added as serial dilutions while keeping the final DMSO concentration constant in each well. As positive control butaprost was used that gave the same maximal effect compared to the maximal effect of $PGE_2$. Cells were incubated together with test compound or butaprost for 4 hours at 37° C. The cAMP release was determined indirectly via luciferase activity that directly correlated to the amount of luciferase enzyme expressed in response to cAMP regulated promoter activity. The luciferase activity was determined by addition of luciferin containing buffer and subsequent quantification of resulting luminescence. Each sample was measured in quadruplicates per experiment and half-maximal effective concentration ($EC_{50}$) and relative maximal effect compared to butaprost was determined from 3 independent experiments with GraphPad Prism Software. A compound that achieved over 80% of the maximal effect of butaprost was considered as full agonist.

For the following compounds the potency was determined in the cAMP release assay applying human EP2 transfectant CHOp6CreLuc-huEP2 cells. All compounds as listed in the table showed full agonistic activity in that assay. The table shows the $-\log EC_{50}=pEC_{50}$ in ranges of 7.9 and 8.9, 9.0 and 9.9 as well as 10.0 and 11.2. The numbers of the compounds correspond to the examples numbers.

EP2 cAMP Release Assay: $pEC_{50}$

| 7.9-8.9 | 9.0-9.9 | 10.0-11.2 |
|---|---|---|
| Example 16, 23, 20, 18, 21 | Example 13, 14, 4, 11, 17, 8, 7, 22 | Example 5, 10, 3, 1, 19, 2, 6, 9, 15 |

Method for Measuring the Inhibition of TNFalpha Release in Human Whole Blood Stimulated with LPS:

Assay was performed with some modifications of the method described by Hatzelmann and Schudt (Hatzelmann and Schudt (2001) JPET 297: 267-279) and the protocol "drawing of venous blood from healthy volunteers for in vitro studies" was approved by the ethics committee of the Landesärztekammer Baden Württemberg in Stuttgart.

Heparinised venous blood was equilibrated to assay conditions for 1 hour at room temperature upon blood drawing. Immediately thereafter, 200 microL whole blood per sample were pre-incubated with 25 microL of a serial dilution of test compound or piclamilast as positive control for 30 min. at 37° C. After pre-incubation blood samples were stimulated by the addition of 25 microL lipopolysaccharide (LPS) (Sigma, Aldrich) per sample resulting in a final concentration of 1 microg/mL LPS and a final volume of 250 microL. Cells were incubated for 4 hours at 37° C. TNFalpha levels were determined from plasma that was obtained by a centrifugation step and transferring the supernatant to a new 96-well plate which was again centrifuged and clear plasma supernatant was used for the measurement of TNFalpha via alphaLISA Technology according to manufacture protocol (Perkin Elmer).

Whole blood samples that were not stimulated with LPS were used as control and set for 100% inhibition. Whole blood samples that were stimulated with LPS and solvent instead of test compound were set as 0% inhibition. Percent inhibition was calculated based on these controls for each sample and since most compounds achieved saturating maximal inhibition of 60% a $pIC_{30}$ value was calculated with GraphPad Prism Software.

For the following compounds the inhibitory values of TNFalpha release [determined as $-\log IC_{30}=pIC_{30}$] in the human whole blood assay between 4.5 and 4.9, between 5.0 and 5.9 and between 6.0 and 6.9 have been determined. The numbers of the compounds correspond to the examples numbers.

Inhibition of LPS Induced TNFalpha Release Assay in Human Whole Blood: $pIC_{30}$

| 4.5-4.9 | 5.0-5.9 | 6.0-6.9 |
|---|---|---|
| Example 3, 4 | Example 15, 22 | Example 10, 1, 19, 2, 9, 13 |

Method for Measuring the Inhibition of TNFalpha Release in Human Peripheral Blood MononuClear Cells (PBMC) Stimulated with LPS:

Assay was performed with some modifications of the method described by Hatzelmann and Schudt (Hatzelmann and Schudt 2001, J. Pharmacol. Exp. Therapeutics 297: 267-279) and the protocol "drawing of venous blood from healthy volunteers for in vitro studies" was approved by the ethics committee of the Landesärztekammer Baden Württemberg in Stuttgart. Peripheral blood mononuclear cells (PBMCs) were isolated from venous blood with the anticoagulant citrate from healthy donors according to standard protocols using Ficoll. The cell layer of PBMCs were washed twice with phosphate buffer solution and equilibrated at room temperature for 60 minutes. 500,000 PBMCs in 180 microL RPMI1640 cell medium supplemented with 10% FCS, NEAA (Non-essential-amino-acids), L-Glutamine and Sodium Pyruvate per sample were pre-incubated with 10 microL of a serial dilution of test compound or piclamilast as positive control for 60 min. at 37° C. After pre-incubation blood samples were stimulated by the addition of 10 microL LPS (Sigma, Aldrich) per sample resulting in a final concentration of 1 ng/mL LPS and a final volume of 200 microL. Cells were incubated for 24 hours at 37° C. TNFalpha levels were determined from cell supernatant that was obtained by a centrifugation step and transferring the supernatant to a new 96-well plate. Content of TNFalpha was determined via alphaLISA Technology according to manufacture protocol (Perkin Elmer).

PBMC samples that were not stimulated with LPS were used as control and set for 100% inhibition. PBMC samples that were stimulated with LPS and solvent instead of test compound were set as 0% inhibition. Percent inhibition was calculated based on these controls for each sample and since most compounds achieved saturating maximal inhibition of 60% a $pIC_{30}$ value was calculated with GraphPad Prism Software.

For the following compounds the inhibitory values of TNFalpha release [determined as $-\log IC_{30}=pIC_{30}$] in human PBMCs between 5.0 and 5.9, between 6.0 and 6.9, between 7.0 and 7.9 and between 8.0 and 9.0 have been determined. The numbers of the compounds correspond to the examples numbers.

Inhibition of LPS Induced TNFalpha Release Assay in Human PBMCs: $pIC_{30}$

| 5.0-5.9 | 6.0-6.9 | 7.0-7.9 | 8.0-9.0 |
|---|---|---|---|
| Example 18 | Example 13, 14, 4, 17, 8, 7, 16, 23, 21 | Example 19, 9, 22 | Example 10, 1, 2, 15 |

Method for Determination of the Inhibition of the Proliferation of Normal Human Lung Fibroblasts (NHLF)

16,500 NHLF-cells were seeded in each well of 24-well cell culture plates and were subsequently cultivated for 3.5 days. Thereafter cell culture medium was replaced by non-serum containing medium and cells were starved for 24 h. Subsequently a serial dilution of test compound was added and cells were stimulated with IL1β (Interleukine 1 beta) (50 pg/mL) and bFGF (basic Fibroblast Growth Factor) (10 ng/mL) for 36 h. For DNA-synthesis (Desoxyribonucleic Acid-synthesis) measurement methyl-$^3$H thymidine was added to the cells for the last 7 h of the 36 h incubation period. Thereafter the radioactive labeled cells were processed for measurement of the incorporated radioactivity as a marker for DNA-synthesis and thus proliferation. For that purpose the cell culture supernatants were removed, adherent cells washed once with ice-cold PBS and fixed in ice-cold 10% (w/v) trichloroacetic acid (TCA) for 30 min. Thereafter TCA was discarded and the DNA of the fixed cells hydrolyzed by administering 0.2 N NaOH. The radioactivity containing NaOH was then transferred into scintillation vials, scintillation liquid added and radioactivity was counted (L56500, Beckman Counter). Test compounds were dissolved in DMSO to a stock concentration of 10 mM. After administration of the compound to the cell cultures the final DMSO concentration was 0.1%. Inhibition of proliferation by the various concentrations of test compound was calculated related to 0.1% DMSO-treated control cells.

For the compounds 1, 2, 9 and 10 $pIC_{50}$ values ($-\log IC_{50}$) between 7.8 and 8.8 have been determined. The numbers of the compounds correspond to the examples numbers.

Method for Determination of the Inhibition of the Myofibroblast Transition of Normal Human Lung Fibroblasts (NHLF)

200,000 NHLF-cells were seeded into each well of six-well cell culture plates in full-medium and starved for 24 h after initial 24 h incubation at 37° C., 5% $CO_2$ and 95% humidity. Before inducing fibroblast-to-myofibroblast conversion by adding 1 ng/mL human TGFβ serial dilution of test compound was administered. After 24 h the cells were collected and processed to lysates as described subsequently.

Cells were washed, twice in PBS, trypsinated and centrifuged at 500×g for 10 min. Afterwards the cell pellet was resuspended in 150 microL freshly prepared lysis buffer (50 mM Hepes, pH 7.5, 150 mM NaCl, 1.5 mM MgCl2, 10% glycine, 1% Triton X-100, 0.5% Desoxycholat, 0.2% SDS, 1 mM EGTA (ethylene glycol tetraacetic acid), 100 mM NaF, 10 mM $Na_4P_2O_7$, 1 mM Na-Vanadat, 1 mM PMSF and 50 U/mL Benzonase (Merck KGaA, Darmstadt, Germany), one Phosphatase Inhibitor Cocktail tablet (Complete Mini from Roche Diagnostics, Mannheim, Germany) per 10 ml buffer and stored at −80° C. for further use. Protein concentration was determined following instructions of the BCA Protein Assay (Pierce Biotechnology, Rockford, Ill., USA). Photometric measurements were performed with the microplate reader Sunrise from Tecan Group Ltd., (Männedorf, Switzerland). 6 μg of protein of the different samples were separated on a 10% SDS (Sodium Dodecyl Sulfate) discontinuous polyacrylamide gel electrophoresis. Thereafter, proteins were blotted from the gel onto a nitrocellulose transfer membrane for 2 h at 400 mA in a wet-blot-chamber. Thereafter the membrane was blocked in 5% milkpowder in PBS (Phosphate Buffered Saline) containing 0.1% Tween 20 at 4° C. overnight. Subsequently the membrane was hybridized for 4 h with the primary anti-Alpha-smooth muscle actin antibody (1:2,000 in 5% milkpowder in PBS), washed three times in PBS containing 0.1% Tween 20. This was followed by incubation with the secondary horseradish-coupled goat anti-mouse IgG detection-antibody (1:10,000 in 5% milkpowder in PBS) for 2 h. After final washing with PBS containing 0.1% Tween 20 (three times for 10 min each) the blot was developed by using a chemiluminescence detection system according to the manufacturer instructions and a luminescent image analyzer (Fuji LAS 1000 Pro).

For the compounds 1, 2, 9 and 10 $pIC_{50}$ values ($-\log IC_{50}$) between 8.5 and 9.5 have been determined. The numbers of the compounds correspond to the examples numbers.

In Vivo Assay: LPS-Induced TNFα Release in Rats

Introduction

Intravenously administration of lipopolysaccharide (LPS) causes a systemic inflammation characterised by release of pro-inflammatory cytokines, e.g. tumor necrosis factor alpha (TNFα). Selective EP2 agonists are administered per oral 1 h prior intravenously LPS challenge in rats. The anti-inflammatory activity of the selective EP2 agonists is assessed based on TNFα levels in blood plasma 1 h after LPS exposure.

Materials and Methods

Animals

Male Sprague Dawley rats weighing 250-300 g were used. Rats were delivered 1 week prior to the experiments and had free access to water and food.

Compound Administration

Compound Preparation

The test compound was mixed with 1.33% polyethylenglycol 400 (PEG400, Merck, Darmstadt, Germany) and subsequently suspended in 2% methocel solution (hypromellose, Sigma, Steinheim, Germany) containing Antifoam C Emulsion (Sigma, Steinheim, Germany, 0.1 mL/15 mL) using a mixing device (ULTRA-TURRAX T8 basic, VDI12, VWR International GmbH). The aimed doses were prepared by dilution series from the stock suspension, which was prepared for the administration of the highest dose in each experiment.

Compound Dosing

The administered volume of the compound suspension is 10 mL/kg. On day of the experiment the rat body weights were documented to calculate the volume to be administered. LPS challenged control animals received drug-free vehicle solution as placebo. Test compounds and vehicle were administered by oral gavage 1 h prior to LPS challenge.

LPS Challenge

LPS (from *Escherichia coli* O55:B5, Sigma, Steinheim, Germany) was solubilised in 0.9% sterile NaCl solution (B. Braun Melsungen AG, Melsungen, Germany) containing 0.1% hydroxylamine (Sigma, Steinheim, Germany). LPS is intravenously (i.v.) injected at a dose of 20 μg/kg (1 mL/kg b.w.) 1 h after compound or vehicle administration.

Determination of TNFα Concentrations

One hour after LPS-challenge, the animals were sacrificed by inhalative isofluran anaesthesia and subsequently cervical dislocation. Heparinised blood was obtained by heart puncture. Blood was centrifuged (21,000×g, 4° C., 10 min), and plasma samples were kept frozen at −20° C. until determination of TNFα levels by ELISA. TNFα was measured with a commercially available ELISA-Kit (Quantikine®, Rat TNFα/TNFSF1A, R&D Systems, Minneapolis, USA).

Data Analysis

The compound effect on TNFα release was calculated individually in percent (%) for each compound treated animal in relation to the mean TNFα level of the vehicle treated LPS-challenged control group:

% effect=(Y−K)/K*100 with defining:
Y=plasma TNFα concentration of the compound treated animal
K=mean plasma TNFα concentration of the vehicle treated group Values less than 0 (negative values) reflected an inhibition of TNFα levels, values exceeding 0 (positive values) displayed an increase of TNFα levels. Statistical analysis was performed on the primary TNFα concentrations by One-Way ANOVA and Dunnett's Multiple Comparison test vs. vehicle treated control group.

The compounds 1, 2, 3, 9 and 10 showed $ED_{50}$ values between 0.1 and 3 mg/kg p.o. The numbers of the compounds correspond to the examples numbers.

In Vivo Assay: LPS-Induced TNFα Release in Mice

Introduction

Intravenously administration of lipopolysaccharide (LPS) causes a systemic inflammation characterised by release of pro-inflammatory cytokines, e.g. tumor necrosis factor alpha (TNFα). Selective EP2 agonists are administered per oral 1 h prior intravenously LPS challenge in mice. The anti-inflammatory activity of the selective EP2 agonists is assessed based on TNFα levels in blood plasma 1 h after LPS challenge.

Materials and Methods

Animals

Female C57BL/6 mice weighing 20-25 g were used. Mice were delivered 1 week prior to the experiments and had free access to water and food.

Compound Administration

Compound Preparation

The test compound was mixed with 1.33% polyethylenglycol 400 (PEG400, Merck, Darmstadt, Germany) and subsequently suspended in 2% methocel solution (hypromellose, Sigma, Steinheim, Germany) using the Covaris S2X System (K Biosciencesdon; United Kingdom). The aimed doses were prepared by dilution series from the stock suspension, which was prepared for the administration of the highest dose in each experiment.

Compound Dosing

The administered volume of the compound suspension is 10 mL/kg. On day of the experiment the mouse body weights were documented to calculate the volume to be administered. LPS challenged control animals received drug-free vehicle solution as placebo. Test compounds and vehicle were administered by oral gavage 1 h prior to LPS challenge.

LPS Challenge

LPS (from *Escherichia coli* 055:B5, Sigma, Steinheim, Germany) was solubilised in 0.9% sterile NaCl solution (B. Braun Melsungen AG, Melsungen, Germany) containing 0.1% hydroxylamine (Sigma, Steinheim, Germany). LPS is intravenously (i.v.) injected at a dose of 100 µg/kg (5 mL/kg b.w.) 1 h after compound or vehicle administration.

Determination of TNFα Concentrations

One hour after LPS-challenge, the animals were sacrificed by inhalative isoflurane anaesthesia and heparinised blood was obtained by retroorbital bleeding. Blood was centrifuged (21,000×g, 4° C., 10 min), and plasma samples were kept frozen at −20° C. until determination of TNFα levels by ELISA. TNFα was measured with a commercially available ELISA-Kit (Quantikine® Immunoassay Mouse TNFα, R&D Systems, Minneapolis, USA).

Data Analysis

The compound effect on TNFα release was calculated individually in percent (%) for each compound treated animal in relation to the mean TNFα level of the vehicle treated LPS-challenged control group:

% effect=(Y−K)/K*100 with defining:
Y=plasma TNFα concentration of the compound treated animal
K=mean plasma TNFα concentration of the vehicle treated group Values less than 0 (negative values) reflected an inhibition of TNFα levels, values exceeding 0 (positive values) displayed an increase of TNFα levels. Statistical analysis was performed on the primary TNFα concentrations by One-Way ANOVA and Dunnett's Multiple Comparison test vs. vehicle-treated control group.

The compounds 1, 2, 3, 9 and 10 showed $ED_{50}$ values between 0.1 and 3 mg/kg p.o. The numbers of the compounds correspond to the examples numbers.

In Vivo Assay: LPS-Induced Pulmonary Inflammation Model in Rats

Introduction

Exposure of rats to aerosolised lipopolysaccharide (LPS) causes a pulmonary mainly neutrophilic inflammation, which can be assessed by bronchoalveolar lavage (BAL). LPS-induced pulmonary inflammation models are robust and are commonly used for the evaluation of test compounds modulating the immediate immune response. Selective EP2 agonists are administered per oral 1 h prior nose-only LPS challenge in rats. The anti-inflammatory activity of the selective EP2 agonists is assessed based on pulmonary total leukocyte and neutrophil counts in the bronchoalveolar lavage fluid 4 h after LPS exposure.

Materials and Methods

Animals

Male Sprague Dawley rats weighing 250-300 g were used. Rats were delivered 1 week prior to the experiments and had free access to water and food.

Compound Administration

Compound Preparation

The test compound was mixed with 1.33% polyethylenglycol 400 (PEG400, Merck, Darmstadt, Germany) and subsequently suspended in 2% methocel solution (hypromellose, Sigma, Steinheim, Germany) containing Antifoam C Emulsion (Sigma, Steinheim, Germany, 0.1 mL/15 mL) using a mixing device (ULTRA-TURRAX T8 basic, VDI12, VWR International GmbH). The aimed doses were prepared by dilution series from the stock suspension, which was prepared for the administration of the highest dose in each experiment.

Compound Dosing

The administered volume of the compound suspension was 10 mL/kg. On day of the experiment the rat body weights were documented to calculate the volume to be administered. LPS challenged and unchallenged control animals received compound-free vehicle solution as placebo. Test compounds and vehicle were administered by oral gavage 1 h prior to LPS challenge.

LPS Challenge

Conscious and restrained animals were connected to a nose-only exposure system (CR equipment SA, Tannay, Switzerland) and were exposed to the LPS aerosol for 30 min. The LPS-containing aerosol was generated using a compressed air driven medication nebulizer device (Pari LC Sprint Star, Pari GmbH, Starnberg, Germany). The LPS solution (*E. coli*, Serotype 055B5, Sigma-Aldrich, 1 mg/ml diluted in PBS) was prepared 30 minutes in advance. The aerosol was dispersed and transported to the exposure tower by a sheath air flow of 600l/h. All rats except negative controls were exposed to LPS.

Bronchoalveolar Lavage 4 hours after LPS challenge, animals were anesthetised by isoflurane and scarified by cervical dislocation. BALs were performed. For the BAL the trachea was exposed and cannulated, followed by gently lavaging the lungs two times in situ with 4 ml PBS buffer supplemented with 0.5% Bovine Serum Albumin (Serve, Darmstadt, Germany).

Total and Differential Cell Counts

Determination of total leukocyte and neutrophil counts in BALF was performed with an automated leukocyte differentiation system (XT-2000iV, Sysmex, Norderstedt, Germany).

Data Analysis

The baseline correction was done for each sample according to the formula:

baseline-corrected cell count value=cell count−median (negative control group)

All further calculations were performed with the baseline-corrected values.

Suppression of LPS-induced total cell and neutrophil influx into the lungs was calculated in % using the medians of the cell counts of each treatment group in relation to the control groups according to the formula:

% effect=$(Y-K)/K*100$

With defining:

Y=median of the baseline-corrected compound treated group

K=median of the baseline-corrected vehicle treated group

Values less than 0 (negative values) reflected an inhibition of neutrophils in BAL, values exceeding 0 (positive values) displayed an increase of neutrophils in BAL. Statistical analysis was performed on the primary cell count data using One-Way ANOVA and Dunnett's Multiple Comparison test vs. positive control.

The compounds 1, 2, 3, 9 and 10 showed $ED_{50}$ values between 0.1 and 2 mg/kg p.o. The numbers of the compounds correspond to the examples numbers.

The invention claimed is:

1. A compound of formula (1)

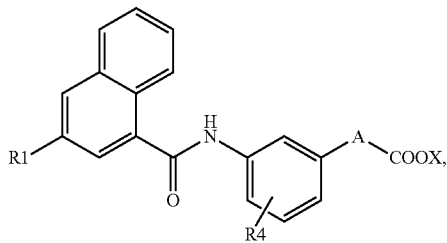

(1)

wherein
A is $-O-CH_2-$, $-CH=CH-$ or $-CH_2-CH_2-$,
X is hydrogen or $C_1$-$C_4$-alkyl,
R1 is unsubstituted phenyl, phenyl substituted by R2 or phenyl substituted by R2 and R3, wherein
R2 is $-(CH_2)_n-OH$, $-(CH_2)_q NH_2$, halogen, $-CH_2-NH(CO)R21$, $-O-(CO)-N(R22)(R23)$ or

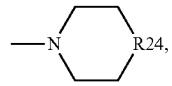

wherein
n is an integer from 0 to 4,
q is an integer from 1 to 4,
R21 is $C_1$-$C_4$-alkyl,
R22 is hydrogen or $C_1$-$C_2$-alkyl,
R23 is hydrogen or $C_1$-$C_2$-alkyl,
R24 is NR25, $CH_2$, O or S
wherein
R25 is hydrogen or $C_1$-$C_2$-alkyl,
R3 is $-(CH_2)_p-OH$,
wherein
p is an integer from 0 to 2, and
R4 is hydrogen or halogen,
or a salt, a solvate, or a solvate of the salt, of formula (1).

2. The compound according to claim 1,
wherein
A is $-O-CH_2-$, $-CH=CH-$ or $-CH_2-CH_2-$,
X is hydrogen or $C_1$-$C_2$-alkyl,
R1 is unsubstituted phenyl, phenyl substituted by R2 or phenyl substituted by R2 and R3, wherein
R2 is $-(CH_2)_n-OH$, $-(CH_2)_q NH_2$, halogen, $-CH_2-NH(CO)R21$, $-O-(CO)-N(R22)(R23)$ or

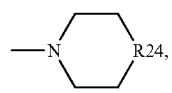

wherein
n is an integer from 0 to 2,
q is 1 or 2
R21 is $C_1$-$C_2$-alkyl,
R22 is hydrogen or $C_1$-$C_2$-alkyl,
R23 is hydrogen or $C_1$-$C_2$-alkyl,
R24 is NR25, $CH_2$, O or S,
wherein
R25 is hydrogen,
R3 is $-(CH_2)_p-OH$,
wherein
p is 0 or 1, and
R4 is hydrogen or halogen.

3. The compound according to claim 1,
wherein
A is $-O-CH_2-$, $-CH=CH-$ or $-CH_2-CH_2-$,
X is hydrogen or $C_1$-$C_2$-alkyl,
R1 is unsubstituted phenyl, phenyl substituted by R2 or phenyl substituted by R2 and R3, wherein
R2 is $-(CH_2)_n-OH$, $-(CH_2)_q NH_2$, halogen, $-CH_2-NH(CO)R21$, $-O-(CO)-N(R22)(R23)$ or

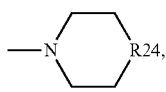

wherein
n is an integer from 0 to 2,
q is 1,
R21 is $C_1$-$C_2$-alkyl,
R22 is $C_1$-$C_2$-alkyl,
R23 is $C_1$-$C_2$-alkyl,
R24 is NR25, $CH_2$, O or S
  wherein
  R25 is hydrogen,
R3 is —$(CH_2)_p$—OH,
  wherein
  p is 0, and
R4 is hydrogen, fluorine, chlorine or bromine.

4. The compound according to claim 3,
wherein
A is —O—$CH_2$—, —CH=CH— or —$CH_2$—$CH_2$—,
X is hydrogen or $C_1$-$C_2$-alkyl,
R1 is unsubstituted phenyl, phenyl substituted by R2 or phenyl substituted by R2 and R3, wherein
  R2 is —$(CH_2)_n$—OH, fluorine, —$CH_2$—NH(CO)R21, —O—(CO)—N(R22)(R23) or

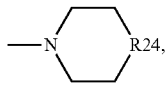

wherein
n is 0 or 1,
R21 is methyl,
R22 is methyl,
R23 is methyl,
R24 is NR25, $CH_2$ or O,
  wherein
  R25 is hydrogen,
R3 is —$(CH_2)_p$—OH,
  wherein
  p is 0, and
R4 is hydrogen, fluorine or chlorine.

5. The compound according to claim 4, which is selected from the group consisting of
(2E)-3-(3-{[(3-phenylnaphthalen-1-yl)carbonyl]amino}phenyl)prop-2-enoic acid,
(2E)-3-(4-fluoro-3-{[(3-phenylnaphthalen-1-yl)carbonyl]amino}phenyl)prop-2-enoic acid,
(2E)-3-(4-chloro-3-{[(3-phenylnaphthalen-1-yl)carbonyl]amino}phenyl) prop-2-enoic acid,
(3-{[(3-phenylnaphthalen-1-yl)carbonyl]amino}phenoxy)acetic acid,
(4-fluoro-3-{[(3-phenylnaphthalen-1-yl)carbonyl]amino}phenoxy)acetic acid,
(4-chloro-3-{[(3-phenylnaphthalen-1-yl)carbonyl]amino}phenoxy)acetic acid,
3-(3-{[(3-phenylnaphthalen-1-yl)carbonyl]amino}phenyl)propanoic acid,
3- (4-fluoro-3-{[(3-phenylnaphthalen-1-yl)carbonyl]amino }phenyl)propanoic acid,
(2E)-3-{3-[({3-[2-fluorophenyl]naphthalen-1-yl}carbonyl)amino]-4fluorophenyl}prop-2-enoic acid,
(2E)-3-{3-[({3-[3-fluorophenyl]naphthalen-1-yl}carbonyl)amino]-4fluorophenyl}prop-2-enoic acid,
(2E)-3-{3-[({3-[4-fluorophenyl]naphthalen-1-yl}carbonyl)amino]-4fluorophenyl}prop-2-enoic acid,
(2E)-3-{3-[({3-[3- (aminomethyl)phenyl]naphthalen-1-yl}carbonyl)amino]-4fluorophenyl}prop-2-enoic acid,
(2E)-3-{4-fluoro-3-[({3-[2-hydroxymethyl)phenyl]naphthalen-1-yl}carbonyl)amino]phenyl}prop-2-enoic acid,
(2E)-3-{4-fluoro-3-[({3-[3-(hydroxymethyl)phenyl]naphthalen-1-yl}carbonyl)amino]phenyl}prop-2-enoic acid,
(2E)-3-[4-fluoro-3-({[3-(3-fluoro-5-hydroxyphenyl)naphthalen-1yl]carbonyl}amino)phenyl]prop-2-enoic acid,
3-[4-fluoro-3-({[3-(2-fluorophenyl)naphthalen-1yl]carbonyl}amino)phenyl]propanoicacid,
3-[4-fluoro-3-({[3-(3-fluorophenyl)naphthalen-1-yl]carbonyl}amino)phenyl]propanoic acid,
(2E)-3-(3-{[(3-{3-[(acetylamino)methyl]phenyl}naphthalen-1-yl)carbonyl]amino }-4 fluorophenyl)prop-2-enoic acid,
(2E)-3-[3-({[3-(3-hydroxyphenyl)naphthalen-1-yl]carbonyl}amino)phenyl]prop-2-enoic acid,
(2E)-3-{3-[({3-[3-(piperazin- 1-yl)phenyl]naphthalen-1-yl}carbonyl)amino]phenyl}prop-2-enoic acid,
(2E)-3-[3-({[3-(morpholin-4-yl)naphthalen-1-yl]carbonyl}amino)phenyl]prop-2-enoic acid,
(2E)-3-[4-fluoro-3-({[3-(piperidin- 1-yl)naphthalen-1-yl]carbonyl}amino)phenyl]prop-2-enoic acid and
(2E)-3-(3-{[(3-{3-[(dimethylcarbamoyl)oxy]phenyl}naphthalen-1-yl)carbonyl]amino}phenyl)prop-2-enoic acid.

6. A pharmaceutical composition comprising
at least one of the compounds according to claim 1, together with at least one pharmaceutically acceptable auxiliary.

7. A fixed combination, non-fixed combination or kit of parts comprising
at least one compound according to claim 1,
at least one therapeutic agent selected from the group consisting of corticosteroids, anticholinergics, β2-adrenoreceptor agonists, H1 receptor antagonists, leukotriene receptor antagonists, 5-lipoxygenase inhibitors, endothelin antagonists, type 4 phosphodiesterase inhibitors, type 5 phosphodiesterase inhibitors, theophylline, PPAR gamma agonists, Angiotensin 1 agonists, immunosuppressants, immune modulators, cytokine inhibitors, vitamin D analogues, HMG-CoA reductase-inhibitors, lung surfactants, antibiotics and any therapeutic with anti-inflammatory, anti-fibrotic or bronchodilatory action, and at least one pharmaceutically acceptable auxiliary.

8. A method of treating an acute or chronic airway disease selected from the group consisting of bronchial asthma, chronic asthmatic disorders with reduced lung function and airway hyperreactivity, bronchial acute exacerbations, chronic bronchitis, acute respiratory distress syndrome, chronic obstructive pulmonary disorder (COPD), pulmonary fibrosis, cystic fibrosis, and pulmonary artery hypertension, comprising administering to a patient in need thereof a therapeutically effective amount of a compound according to claim 1.

9. The compound according to claim 1, wherein the compound is
(2E)-3-(3-{[(3-phenylnaphthalen-1-yl)carbonyl]amino}phenyl)prop-2-enoic acid or a salt thereof.

10. The compound according to claim 1, wherein the compound is (2E)-3-(4-fluoro-3-{[(3-phenylnaphthalen-1-yl)carbonyl]amino}phenyl)prop-2-enoic acid or a salt thereof.

11. The compound according to claim 1, wherein the compound is (2E)-3-{3-[({3-[2-fluorophenyl]naphthalen-1-yl}carbonyl)amino]-4-fluorophenyl}prop-2-enoic acid or a salt thereof.

12. The compound according to claim 1, wherein the compound is (2E)-3-{3-[({3-[3-fluorophenyl]naphthalen-1-yl}carbonyl)amino]-4-fluorophenyl}prop-2-enoic acid or a salt thereof.

13. A pharmaceutical composition comprising the compound according to claim 9 together with at least one pharmaceutically acceptable auxiliary.

14. A pharmaceutical composition comprising the compound according to claim 10 together with at least one pharmaceutically acceptable auxiliary.

15. A pharmaceutical composition comprising the compound according to claim 11 together with at least one pharmaceutically acceptable auxiliary.

16. A pharmaceutical composition comprising the compound according to claim 12 together with at least one pharmaceutically acceptable auxiliary.

17. A method of treating an acute or chronic airway disease selected from the group consisting of bronchial asthma, chronic asthmatic disorders with reduced lung function and airway hyperreactivity, bronchial acute exacerbations, chronic bronchitis, acute respiratory distress syndrome, chronic obstructive pulmonary disorder (COPD), pulmonary fibrosis, cystic fibrosis, and pulmonary artery hypertension comprising administering to a patient in need thereof a therapeutically effective amount of the compound according to claim 9.

18. A method of treating an acute or chronic airway disease selected from the group consisting of bronchial asthma, chronic asthmatic disorders with reduced lung function and airway hyperreactivity, bronchial acute exacerbations, chronic bronchitis, acute respiratory distress syndrome, chronic obstructive pulmonary disorder (COPD), pulmonary fibrosis, cystic fibrosis, and pulmonary artery hypertension comprising administering to a patient in need thereof a therapeutically effective amount of the compound according to claim 10.

19. A method of treating an acute or chronic airway disease selected from the group consisting of bronchial asthma, chronic asthmatic disorders with reduced lung function and airway hyperreactivity, bronchial acute exacerbations, chronic bronchitis, acute respiratory distress syndrome, chronic obstructive pulmonary disorder (COPD), pulmonary fibrosis, cystic fibrosis, and pulmonary artery hypertension comprising administering to a patient in need thereof a therapeutically effective amount of the compound according to claim 11.

20. A method of treating an acute or chronic airway disease selected from the group consisting of bronchial asthma, chronic asthmatic disorders with reduced lung function and airway hyperreactivity, bronchial acute exacerbations, chronic bronchitis, acute respiratory distress syndrome, chronic obstructive pulmonary disorder (COPD), pulmonary fibrosis, cystic fibrosis, and pulmonary artery hypertension comprising administering to a patient in need thereof a therapeutically effective amount of the compound according to claim 12.

* * * * *